US012611387B2

(12) United States Patent
Rubinstenn et al.

(10) Patent No.: US 12,611,387 B2
(45) Date of Patent: Apr. 28, 2026

(54) COMPOUND AND COMPOSITION FOR INDUCING NEUROPROTECTION

(71) Applicants: REST THERAPEUTICS, Paris (FR); UNIVERSITE DE MONTPELLIER, Montpellier (FR); INSTITUT NATIONAL DE LA SANTE ET DE LA RECHERCHE MEDICALE, Paris (FR); ECOLE PRATIQUE DES HAUTES ETUDES, Paris (FR)

(72) Inventors: Gilles Rubinstenn, Paris (FR); Tangui Maurice, Saint-Gely-du-Fesc (FR)

(73) Assignees: REST THERAPEUTICS, Paris (FR); UNIVERSITE DE MONTPELLIER, Montpellier (FR); INSTITUT NATIONAL DE LA SANTE ET DE LA RECHERCHE MEDICALE, Paris (FR); ECOLE PRATIQUE DES HAUTES ETUDES, Paris (FR)

( * ) Notice: Subject to any disclaimer, the term of this patent is extended or adjusted under 35 U.S.C. 154(b) by 621 days.

(21) Appl. No.: 17/924,420

(22) PCT Filed: May 20, 2021

(86) PCT No.: PCT/FR2021/050929
§ 371 (c)(1),
(2) Date: Nov. 10, 2022

(87) PCT Pub. No.: WO2021/234324
PCT Pub. Date: Nov. 25, 2021

(65) Prior Publication Data

US 2023/0270695 A1 Aug. 31, 2023

(30) Foreign Application Priority Data

May 20, 2020 (FR) .................................. FR2005138

(51) Int. Cl.
*A61K 31/136* (2006.01)
*A61P 39/06* (2006.01)

(52) U.S. Cl.
CPC ............ *A61K 31/136* (2013.01); *A61P 39/06* (2018.01)

(58) Field of Classification Search
CPC .. A61K 2300/00; A61K 31/13; A61K 31/136; A61K 31/14; A61K 45/06; A61P 25/08; A61P 25/28; A61P 25/32; A61P 29/00; A61P 39/06; A61P 9/10; A61P 25/00
See application file for complete search history.

(56) References Cited

U.S. PATENT DOCUMENTS 9,714,212 B2 * 7/2017 Guerret ................. C07C 211/38

FOREIGN PATENT DOCUMENTS

| | | | | |
|---|---|---|---|---|
| WO | 2009062391 A1 | | 5/2009 | |
| WO | 2013064579 A1 | | 5/2013 | |
| WO | 2014191424 A1 | | 12/2014 | |
| WO | 2017191034 A1 | | 11/2017 | |
| WO | 2019115833 A1 | | 6/2019 | |
| WO | WO-2020232246 A1 | * | 11/2020 | ............. A61K 33/14 |

OTHER PUBLICATIONS

Alzheimer's Association, https://www.alz.org/alzheimers-dementia/research-and-progress/prevention, 2025 (Year: 2025) (Year: 2025).*
Berryhill, Cognitive Disorders, 2012 (Year: 3023).*
Gloriane et al. (The J for Nurse Practitioners, 2017, p. 129-135). (Year: 2017).*
https://www.mayoclinic.org/diseases-conditions/alzheimers-disease/expert-answers/alzheimers-prevention/faq-20058140, p. 1, title, para 1, 2024 (Year: 2024).*
International Search Report in PCT/FR2021/050929; Mailing Date: Sep. 8, 2021 (with English translation), 10 pages.
Arndt, J.W., Qian, F., Smith, B.A et al. Structural and kinetic basis for the selectivity of aducanumab for aggregated forms of amyloid-β. Sci Rep 8, 6412 (2018), pp. 1-16.
Beaurain M., Salabert A.S., Ribeiro M.J., Arlicot N., Damier P., Le Jeune F., Demonet J.F., Payoux P. Innovative Molecular Imaging for Clinical Research, Therapeutic Stratification, and Nosography in Neuroscience. Frontiers in Medicine, 2019, 6:268, pp. 1-32.
Creeley C, Wozniak DF, Labruyere J, Taylor GT, Olney JW. Low doses of memantine disrupt memory in adult rats. J Neurosci. 2006;26(15):3923-3932. doi:10.1523/JNEUROSCI.4883-05.2006.

(Continued)

*Primary Examiner* — Umamaheswari Ramachandran
(74) *Attorney, Agent, or Firm* — Steven J. Solomon

(57) ABSTRACT

The invention relates to a compound of formula (I) or a pharmaceutically acceptable salt thereof for use in inducing neuroprotection, in a subject in need thereof. The compound or a pharmaceutically acceptable salt thereof can be used in inducing neuroprotection in a subject suffering from, suspected of suffering from, or considered to be at risk of suffering from a neurodegenerative pathology. The compound or a pharmaceutically acceptable salt thereof also can be used in preventing or treating a neurodegenerative pathology, and/or in preventing or decreasing cognitive impairment in a subject suffering from, suspected of suffering from, or considered to be at risk of suffering from a neurodegenerative pathology.

6 Claims, 8 Drawing Sheets

Figure 1:
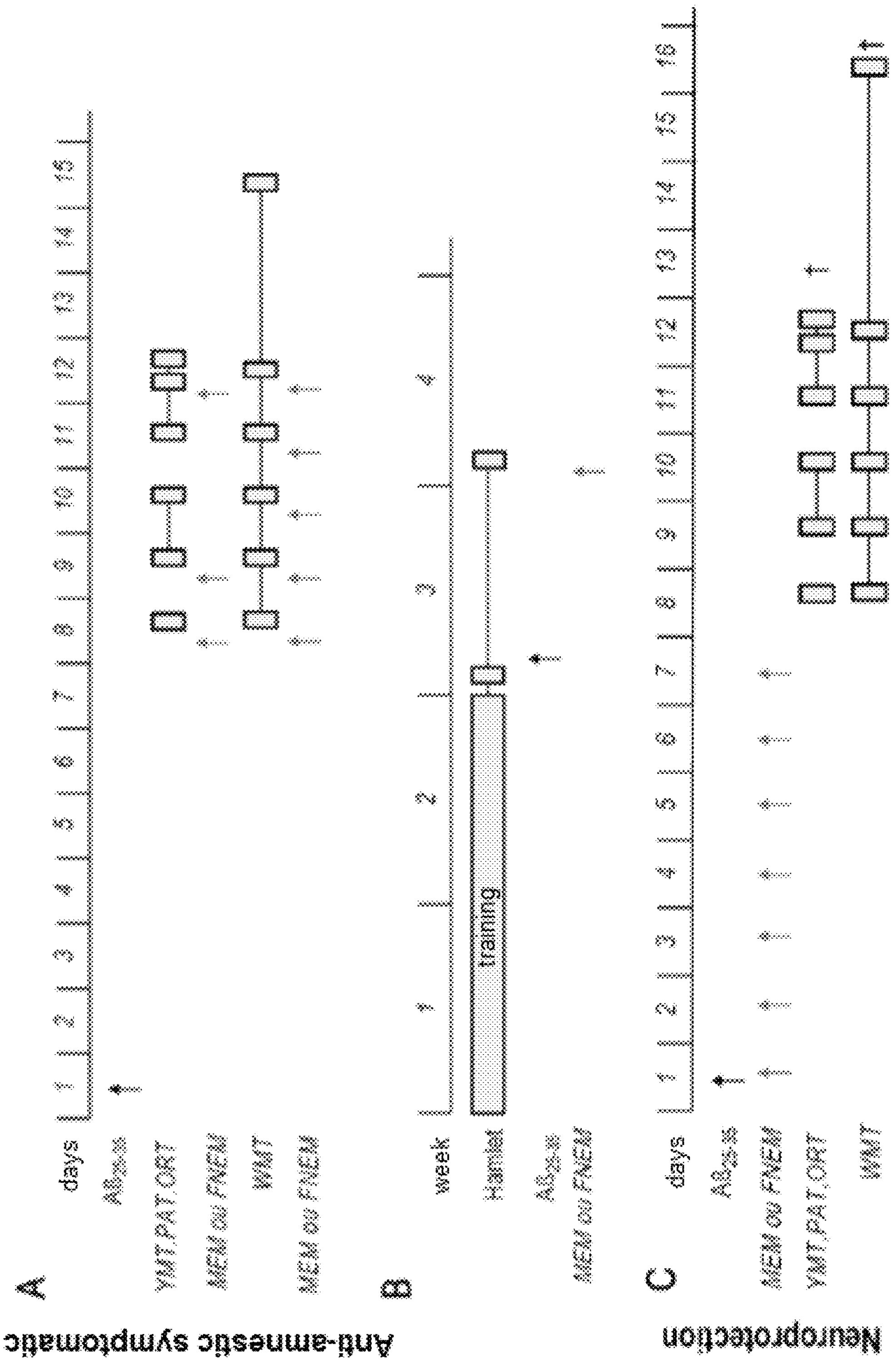

Specification includes a Sequence Listing.

(56) References Cited

OTHER PUBLICATIONS

Knight R, Khondoker M, Magill N, Stewart R, Landau S: A Systematic Review and Meta-Analysis of the Effectiveness of Acetylcholinesterase Inhibitors and Memantine in Treating the Cognitive Symptoms of Dementia. Dement Geriatr Cogn Disord 2018;45:131-151. doi: 10.1159/000486546.
Liu, Chia-Chen, et al. Apolipoprotein E and Alzheimer disease: risk, mechanisms and therapy. Nat Rev Neurology 9, Jan. 8, 2013; pp. 106-118.
Meunier J, Ieni J, Maurice T. The anti-amnesic and neuroprotective effects of donepezil against amyloid β25-35 peptide-induced toxicity in mice involve an interaction with the 1 receptor. Br J Pharmacol. 2006;149: 998-1012.
Rodríguez Cruz Y, Strehaiano M, Rodriguez Obaya T, Garcia Rodriguez JC, Maurice T. An intranasal formulation of erythropoietin (Neuro-EPO) prevents memory deficits and amyloid toxicity in the APPSwe transgenic mouse model of Alzheimer's disease. J Alz Dis. 2017;55:231-248 (submitted as uncorrected author proof, pp. 1-18).
Villard V, Espallergues J, Keller E, Alkam T, Nitta A, Yamada K, Nabeshima T, Vamvakides A, Maurice T. Anti-amnesic and neuroprotective effects of the aminotetrahydrofuran derivative ANAVEX1-41 against amyloid ß25-35—induced toxicity in mice. Neuropsychopharmacology. 2009 34:1552-66 (submitted as web publication pp. 1-15).
Villard V, Espallergues J, Keller E, Vamvakides A, Maurice T. Anti-amnesic and neuroprotective potentials of the mixed muscarinic receptor/sigma1 (01) ligand ANAVEX2-73, a novel aminotetrahydrofuran derivative. J Psychopharmacol. 2011; 25, title page and pp. 1-17.

* cited by examiner

COMPOUND AND COMPOSITION FOR INDUCING NEUROPROTECTION

The invention relates to the field of neurodegenerative diseases.

The invention relates to a compound of formula (I) for use in inducing neuroprotection, in a subject in need thereof.

The invention further relates to a combination comprising the compound of formula (I) and at least one other compound such as, but not limited to, a connexin modulator, an acetylcholinesterase inhibitor, a positive modulator of sigma-1 receptors, or an antibody for combatting amyloid plaque formation or Tau protein hyperphosphorylation.

PRIOR ART

The World Health Organisation (WHO) estimates that by 2050, the number of people aged over 60 will reach two billion. This unprecedented ageing of the world's population suggests strong pressure on health systems due to age-related chronic diseases. Dementia is one such diseases. For example, the WHO estimates that the total number of people with dementia will exceed 150 million by 2050.

Dementia is characterised by a deterioration in cognitive functions, particularly memory and reasoning, which affects the patient's behaviour and ability to perform everyday tasks. Dementia is a syndrome that encompasses a wide range of pathologies that affect different areas of the brain and/or other regions of the central nervous system and in particular involve neurodegeneration and neuronal cell death. Directly linked to ageing, mitochondrial dysfunction and oxidative stress play a crucial role in the pathogenesis of neurodegenerative diseases. These diseases are also often linked to an abnormal accumulation of certain proteins and/or accumulation of mutated and/or abnormally folded proteins as seen in Aβ amyloidoses, tauopathies, synucleinopathies, and aggregation of superoxide dismutase-1 (SOD1), polyglutamine, or TDP-43 protein. Not all neurodegenerative diseases involve a deterioration of cognitive abilities in their early stages. The symptoms can in particular be primarily motor symptoms. Moreover, they are not all linked to ageing, in particular when they are linked to genetic mutations or traumatic accidents.

Alzheimer's disease is the most common form of the neurodegenerative pathologies and accounts for 60-70% of dementia cases. Other common forms of neurodegenerative pathologies in particular include vascular dementia, dementia with Lewy bodies (Parkinson's dementia), frontotemporal dementia (degeneration of the frontal lobes of the brain), Huntington's disease, posterior cortical atrophy, Parkinson's disease, amyotrophic lateral sclerosis, and stroke.

Excitotoxicity is commonly observed in neuronal tissues in the presence of acute and chronic neurological disorders, such as the aforementioned neurodegenerative pathologies, as well as with spinal cord injuries, head injuries, alcoholism and alcohol withdrawal (Korsakoff syndrome). Excitotoxicity corresponds to the overactivation of glutamate receptors selectively activated by N-methyl-D-aspartate receptors (NMDA receptors), which leads to neuronal cell death by apoptosis, in particular, but in a non-limiting manner, in connection with the massive influx of calcium into cells and which leads to mitochondrial dysfunction.

NM DA receptor blocking agents are thus known to be neuroprotective in various acute neurotoxicity models. WO 2009/062391 describes such antagonists including memantine. However, the doses required to achieve the neuroprotective effect are such that adverse side effects, even effects contrary to the expected effect on memory abilities, make these molecules unusable in humans. To date, memantine (3,5-Dimethyl-1-adamantanamine), a non-competitive inhibitor of NMDA channels, is the only compound in this class to have been authorised by certain national health agencies for the symptomatic treatment of mild to moderately severe forms of Alzheimer's disease, in order to treat cognitive disorders linked to Alzheimer's disease. However, in humans, the effects thereof in treating symptoms only appear limited. In October 2016, meta-analyses of clinical data showing, at the authorised dosage, that the efficacy is, at best, modest, established only in the short term, and mainly on cognitive dysfunctions, led the French National Health Authority (HAS) to rule that the clinical relevance of these effects has not been clearly established. This led to the delisting of this molecule in 2018 due to: (i) the lack of clinical relevance of its symptomatic effects, (ii) the lack of demonstration of its efficacy on behavioural disorders, quality of life, time to enter an institution, mortality, disease progression, and burden of illness for caregivers, (iii) its safety profile and (iv) the high risk of drug interactions in elderly subjects. These modest effects of memantine are reported in various meta-analyses (e.g. Knight et al., 2018).

This low efficacy could be explained by the insufficient doses administered to obtain an effective concentration in the central nervous system corresponding to the $IC_{50}$ values observed in vitro for the molecule (Valis et al. 2019). However, the side effects of memantine, in particular the amnestic and neuropsychiatric adverse effects thereof, but also adverse side effects such as digestive and cardiovascular disorders, do not allow the doses administered to be increased. Moreover, some authors have shown, in animal models, that the effects against neurotoxicity were only observed at doses of memantine that induced severe neurobehavioural disorders, in particular severe sensorimotor impairment as well as significant memory impairment (Creeley et al., 2006).

However, moderate NMDA receptor inhibitors are still prime candidates for treating neurodegeneration. There is thus a strong need for such an inhibitor that could be used at doses that would allow effective doses to be obtained in the cerebrospinal fluid (CSF) to induce inhibition of neurotoxicity in patients, without unacceptable adverse effects and without worsening cognitive symptoms. More specifically, NM DA receptors, like other glutamate receptors, also play a role in neural plasticity; thus, while agents blocking these receptors do not prevent synaptic transmission, it is known that some prevent the triggering of long-term potentiation: as the dose of the antagonist is increased, synaptic plasticity decreases and memory deficits increase.

Different NMDA receptor antagonists are also known to have different modes of action, such that it is difficult to predict the effects from one antagonist to another, and from one type of pathology to another, even for molecules with a similar structure.

The WO 2014/191424 application describes 2-fluoroethyl normemantine (3-(2-fluoroethyl)adamantan-1-amine, FENM) labelled $^{18}F$ for the labelling of NMDA receptors and their imaging by positron emission tomography to study the distribution of these receptors and the response thereof to drug treatments or in the development of neurodegenerative diseases. This application describes an affinity of FENM for NMDA receptors of an order of magnitude that is similar to that of memantine.

The WO 2019/115833 application describes FENM in the treatment of anxiety and depression disorders.

The WO 2013/064579 application describes a combination of a connexin-blocking agent (such as meclofenamic acid) with an acetylcholinesterase inhibitor (such as donepezil) for use in treating cognitive disorders. However, it should be noted that acetylcholinesterase inhibitors, initially authorised for the symptomatic treatment of Alzheimer's disease, have also been delisted in France due to the low efficacy thereof.

Patients today are thus faced with a lack of any convincing therapeutic solution capable of inducing neuroprotection in the context of neurodegeneration or acute neuronal impairment.

Technical Problem

The purpose of the invention is thus to overcome the drawbacks of the prior art. In particular, the invention aims to propose a compound for use in neuroprotection; said compound having a neuroprotective effect preventing the mechanisms of neuronal cell death and maintaining the cognitive abilities of subjects suffering from pathologies that are in particular linked to excitotoxicity, but not limited thereto. Moreover, the present invention aims to propose a compound that does not exhibit harmful effects on cognition such as those observed for NM DA receptor inhibitors, thereby safely expanding the range of doses that can be administered to humans for the symptomatic treatment of Alzheimer's disease. Finally, the present invention aims to propose a compound that is effective in the symptomatic treatment of the cognitive disorders induced by neurodegeneration.

BRIEF DESCRIPTION OF THE INVENTION

The applicants have surprisingly found that FENM possesses significant neuroprotective effects that memantine lacks, and which prevent cell death mechanisms and result in maintaining cognitive abilities in a mouse model comprising intracerebral administration of amyloid-$\beta_{25}$-35 ($A\beta_{325}$-35) peptide oligomers. Moreover, the applicants have demonstrated that FENM does not have the harmful effects that memantine has on memory. This makes it possible to envisage administration at higher doses than those authorised for memantine and thus expect a gain in effectiveness. Finally, it was found that FENM is also more effective than memantine in the symptomatic treatment of the cognitive disorders induced by neurodegeneration.

Thus, one purpose of the present invention is to propose a compound of formula (I):

(I)

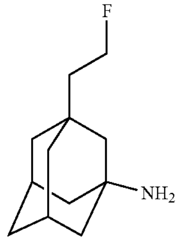

or a pharmaceutically acceptable salt thereof for use in inducing neuroprotection, in a subject in need thereof.

According to an optional feature, the pharmaceutically acceptable salt corresponds to the formula (II):

(II)

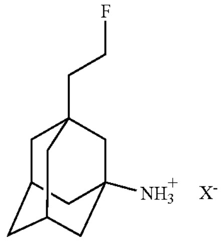

wherein $X^-$ denotes a counteranion selected from the group consisting of chloride, bromide, iodide, acetate, methane sulphonate, benzene sulphonate, camphosulphonate, tartrate, dibenzoate, ascorbate, fumarate, citrate, phosphate, salicylate, oxalate, bromohydrate, and tosylate ions.

The inventors have found that FENM induces significant protection against the various components of neurodegeneration, and thus:

- according to one aspect of the invention, the neuroprotection procured by the compounds of the invention includes the prevention or reduction of neuroinflammation;
- according to another aspect of the invention, the neuroprotection procured by the compounds of the invention includes the prevention or reduction of oxidative stress in neuronal cells;
- according to one aspect of the invention, the neuroprotection procured by the compounds of the invention includes the prevention or reduction of neuronal apoptosis in said subject.

This neuroprotection can have a positive effect on brain structures, and in particular those involved in cognitive processes. According to one aspect of the invention, the neuroprotection procured by the compounds of the invention includes the inhibition of hippocampal cell loss in said subject. Changes in the structure and volume of the hippocampus are detected by medical imaging and can be used to monitor the efficacy of the treatment.

The neuroprotection procured by the compounds of formula (I) further results in the preservation of the subject's cognitive abilities. Thus, according to one aspect of the invention, the neuroprotection procured by the compounds of the invention includes the prevention or reduction of impairments to the subject's cognitive abilities, in particular, the prevention or reduction of impairments:

- to the subject's short-term memory,
- to the subject's intermediate-term memory,
- to the subject's spatial memory, or
- to the subject's recognition and/or learning abilities.

The compounds of formula (I) are particularly effective in inducing neuroprotection against the toxicity of toxic protein aggregates, such as oligomerised $A\beta_{25-35}$. Thus, according to one aspect of the invention, neuroprotection includes protection against the toxicity of β-amyloid aggregates, of its fragments or of its oligomers, in said subject.

The neuroprotection procured by the compounds of formula (I) make it possible to fight the mechanisms underlying numerous neurodegenerative pathologies. Thus, according to one aspect, the invention further relates to the compound of formula (I) for use in a subject suffering from, suspected of suffering from, or considered to be at risk of suffering from a pathology of the central nervous system selected from tauopathies, synucleinopathies, amyloidopathies, Alzheimer's disease, Parkinson's disease, multiple system atrophy, Huntington's disease, posterior cortical atrophy, Pick's disease, epilepsy, vascular dementia, frontotemporal dementia, dementia with Lewy bodies, amyotrophic lateral sclerosis, Korsakoff's syndrome, alcohol withdrawal, ischaemia, neonatal ischaemia, head injury, or stroke, preferably Alzheimer's disease.

Because of the putative mode of action thereof, the compound of formula (I) is particularly adapted for use in combination with compounds targeting other aspects or pathways involved in neurodegenerative processes. One purpose of the present invention is thus to propose a combination of the compound of formula (I) with:

- at least one acetylcholinesterase inhibitor, preferably selected from donepezil, rivastigmine, galantamine, or a pharmaceutically acceptable salt thereof,
- at least one connexin inhibitor, preferably selected from meclofenamic acid, enoxolone, mefloquine and 2-amino ethoxy diphenyl borate (APB), or a pharmaceutically acceptable salt thereof,
- aducanumab or an antigen-binding fragment thereof capable of fighting against the toxicity of β-amyloid aggregates, its fragments or its oligomers, or
- at least one positive modulator of sigma-1 receptors such as those described in the WO 2017191034 application or a pharmaceutically acceptable salt thereof, preferably selected from 2-(2-chlorophenyl)-2-oxo-3,3,5,5-tetramethyl-[1,4,2]-oxazaphosphinane; 2-(4-chlorophenyl)-2-oxo-3,3,5,5-tetramethyl-[1,4,2]-oxazaphosphinane; 2-(3,5-dichlorophenyl)-2-oxo-3,3,5,5-tetramethyl-[1,4,2]-oxazaphosphinane; 2-(2,3-dichlorophenyl)-2-oxo-3,3,5,5-tetramethyl-[1,4,2]-oxazaphosphinane; 2-(3-Fluorophenyl)-2-oxo-3,3,5,5-tetramethyl-[1,4,2]-oxazaphosphinane; 2-(4-Fluorophenyl)-2-oxo-3,3,5,5-tetramethyl-[1,4,2]-oxazaphosphinane; 2-(3-nitrophenyl)-2-oxo-3,3,5,5-tetramethyl-[1,4,2]-oxazaphosphinane; 2-(4-benzyloxycarbamoylphenyl)-2-oxo-3,3,5,5-tetramethyl-[1,4,2]-oxazaphosphinane; 2-(pyridin-2-yl)-2-oxo-3,3,5,5-tetramethyl-[1,4,2]-oxazaphosphinane; 2-(pyridin-3-yl)-2-oxo-3,3,5,5-tetramethyl[1,4,2]-oxazaphosphinane; 2-(pyridin-4-yl)-2-oxo-3,3,5,5-tetramethyl[1,4,2]-oxazaphosphinane; 2-(pyrimidin-2-yl)-2-oxo-3,3,5,5-tetramethyl-[1,4,2]-oxazaphosphinane; 2-(pyrimidin-5-yl)-2-oxo-3,3,5,5-tetramethyl-[1,4,2]-oxazaphosphinane; 2-(3-aminophenyl)-2-oxo-3,3,5,5-tetramethyl-[1,4,2]-oxazaphosphinane; 2-(4-aminophenyl)-2-oxo-3,3,5,5-tetramethyl-[1,4,2]-oxazaphosphinane; 2-(3-chlorophenyl)-N-methyl-2-oxo-3,3,5,5-tetramethyl-[1,4,2]-oxazaphosphinane; 2-(3-chlorophenyl)-2-thiono-3,3,5,5-tetramethyl-[1,4,2]-oxazaphosphinane; 2-(3-chlorophenyl)-2-oxo-3,3,5,5-tetramethyl-[1,4,2]-oxazaphosphinane; 2-morpholin-4-ylethyl 1-phenylcyclohexane-1-carboxylate); (+)-pentazocine; 1,13-dimethyl-10-prop-2-enyl-10-azatricyclo[7.3.1.02,7]trideca-2(7),3,5-trien-4-ol; 1-[2-(3,4-dimethoxyphenyl)ethyl]-4-(3-phenylpropyl) piperazine; 1-(2,2-diphenyltetrahydro-3-furanyl)-N,N-dimethylmethanamine; 2-{[(E)-{5-methoxy-1-[4-(trifluoromethyl)phenyl]pentylidene]amino] oxy}ethanamine; N-(1-benzylpiperidin-4-yl)-4-iodobenzamide; (5E)-N-(cyclopropylmethyl)-N-methyl-3,6-diphenyl-5-hexen-3-amine; 1-{3-[4-(3-chlorophenyl)-1-piperazinyl]propyl}-5-methoxy-3,4-dihydro-2(1H)-quinolinone; (1S,2R)-N-[2-(3,4-dichlorophenyl)ethyl]-N-methyl-2-(1-pyrrolidinyl) cyclohexanamine); 6-[(4-benzylpiperazin-1-yl) methyl]-2,3-dimethoxyphenol); 4-(3-(methylsulfonyl) phenyl)-1-propylpiperidine or a pharmaceutically acceptable salt thereof, preferably 2-(3-chlorophenyl)-2-oxo-3,3,5,5-tetramethyl-[1,4,2]-oxazaphosphinane or 2-morpholin-4-ylethyl 1-phenylcyclohexane-1-carboxylate or a pharmaceutically acceptable salt thereof.

According to a particular aspect, the invention relates to said combination for use to induce neuroprotection, in a subject in need thereof, in particular a subject suffering from, suspected of suffering from or at risk of suffering from an aforementioned pathology of the central nervous system, and particularly a subject suffering from, suspected of or at risk of suffering from Alzheimer's disease.

The activity profile of the compound of formula (I) shows neuroprotection over large dose ranges, without harmful effects on the cognitive abilities of the treated subjects. Higher doses than those currently permitted for memantine are thus possible, resulting in a more effective treatment. According to another aspect, the invention thus relates to the compound of formula (I) for inducing neuroprotection in a subject in need thereof, said compound being administered orally at a dose greater than 20 mg per day, preferably greater than or equal to 30 mg per day, optionally within a combination as described hereinabove.

Other advantages and features of the invention will appear upon reading the following description, which is given as a rough guide and in no way as a limiting guide, with reference to the accompanying Figures, which show:

FIGURES

FIG. 1, experimental designs for the administration of the oligomerised $A\beta_{25-35}$ peptide, test compounds and the performance of behavioural tests to evaluate the cognitive abilities of the animals. (A, B) Evaluation of the symptomatic effects on amnesia induced by the oligomerised $A\beta_{25-35}$ peptide. (C) Evaluation of the neuroprotective effect of the test compounds. YMT, Y-Maze Test; PAT, Passive Avoidance Test; ORT, Object Recognition Test; WMT, Morris Water Maze Test; t, sacrifice; black arrow: intracerebroventricular injection of oligomerised $A\beta_{25-35}$ peptide; grey arrows: administration of test compounds/vehicle.

Figure 2:
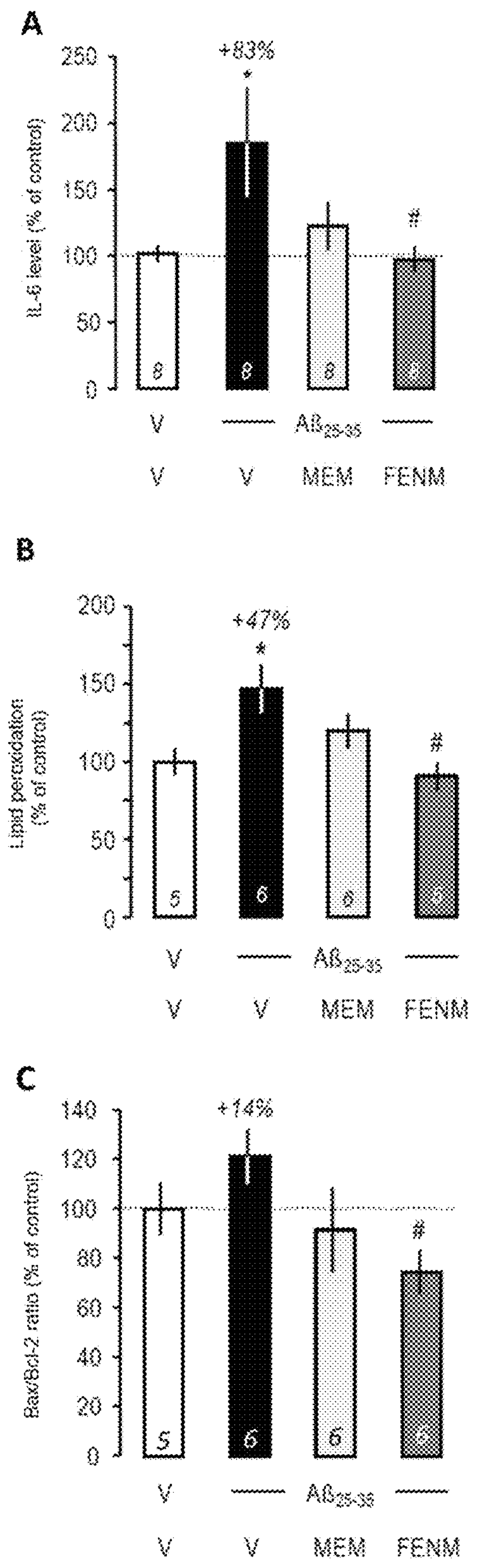

FIG. 2, effect of memantine (MEM) and of FENM (0.3 mg/Kg i.p.), on levels of interleukin-6 (IL-6) (A), lipid peroxidation (B), or Bax/BcI-2 ratio (C) in hippocampal homogenates from mice intoxicated or not with oligomerised $A\beta_{25-35}$ peptide. ANOVA: A, $F_{(3,22)}=2.53$, $p>0.05$; B, $F_{(3,21)}=4.33$, $p<0.05$; C, $F_{(3,22)}=0.763$, $p>0.05$.* $p<0.05$, *** $p<0.001$ vs. (V+V); #$p<0.05$ vs. (V+$A\beta_{25-35}$); Dunnett's test. The number of mice per group is indicated in each column. V: vehicle solution. The percentage increase induced by oligomerised $A\beta_{25-35}$ compared to the untreated, non-intoxicated control group (V+V) is shown above the columns.

Figure 3:
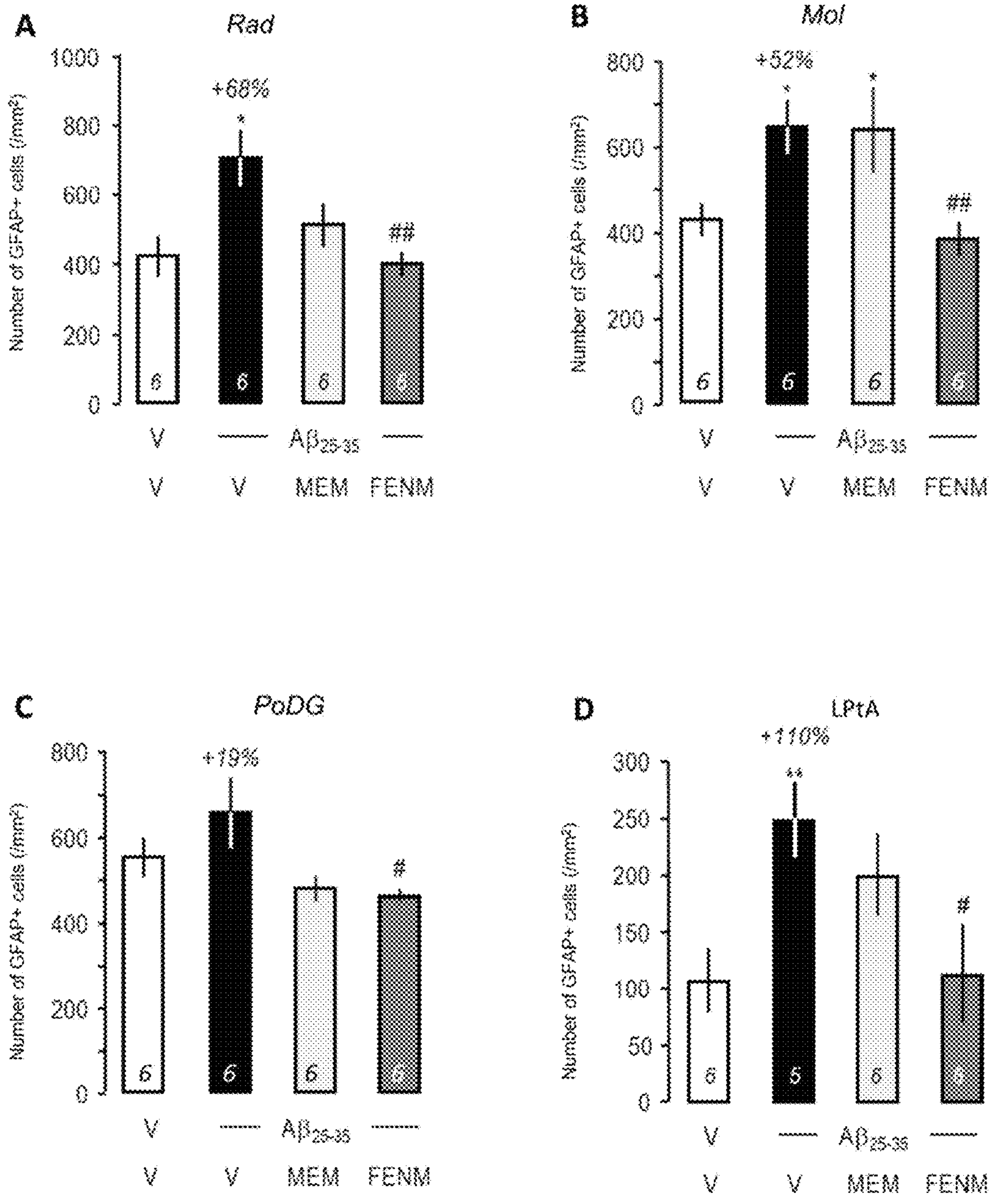

FIG. 3, effect of memantine (MEM) and of FENM (0.3 mg/Kg i.p.), on the astroglial response following the administration of oligomerised $A\beta_{25-35}$ peptide. Immunohistochemical quantification of GFAP in the stratum radiatum (A, Rad), stratum moleculare (B, Mol), polymorphic layer of the dentate gyrus (C, PoDT) of the hippocampus and the lateral parietal association area (D, LPTA) ANOVA: A, $F_{(3,22)}=5.06$, $p<0.01$; B, $F_{(3,23)}=4.50$, $p<0.05$; C, $F_{(3,23)}=3.24$, $p<0.05$; D, $F_{(3,22)}=3.71$, $p<0.05$. * $p<0.05$, vs. (V+V); #$p<0.05$, ##$p<0.01$ vs. ($A\beta_{25-35}$+V); Dunnett's test. V: vehicle solution. The number of mice per group is indicated in each column. The percentage increase induced by oligomerised $A\beta_{25-35}$ compared to the untreated, non-intoxicated control group (V+V) is shown above the columns.

Figure 4:
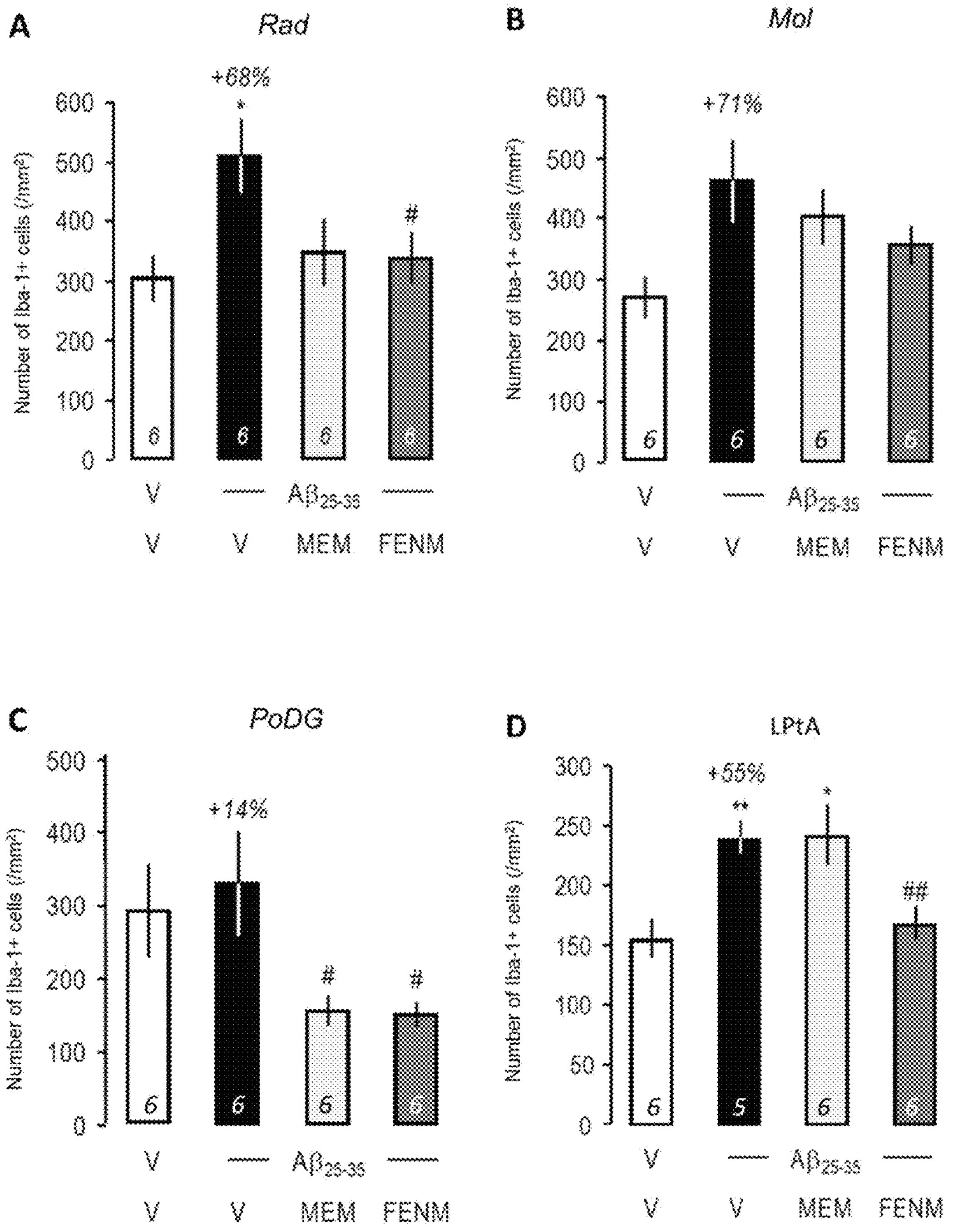

FIG. 4, effect of memantine (MEM) and of FENM (0.3 mg/Kg i.p.), on the microglial response following the administration of oligomerised $A\beta_{25-35}$ peptide. Immunohistochemical quantification of the Iba-1 marker in the stratum radiatum (A, Rad), stratum moleculare (B, Mol), polymorphic layer of the dentate gyrus (C, PoDT) of the hippocampus and the lateral parietal association area (D, LPTA) ANOVA: A, $F_{(3,23)}=3.22$, $p<0.05$; B, $F_{(3,22)}=2.86$, $p>0.05$; C, $F_{(3,23)}=3.38$, $p<0.05$; D, $F_{(3,23)}=6.43$, $p<0.01$. * $p<0.05$, ** $p<0.01$ vs. (V+V); #$p<0.05$, ##$p<0.01$ vs. ($A\beta_{25-35}$+V); Dunnett's test. V: vehicle solution. The number of mice per group is indicated in each column. The percentage increase induced by oligomerised $A\beta_{25-35}$ compared to the untreated, non-intoxicated control group (V+V) is shown above the columns.

Figure 5:
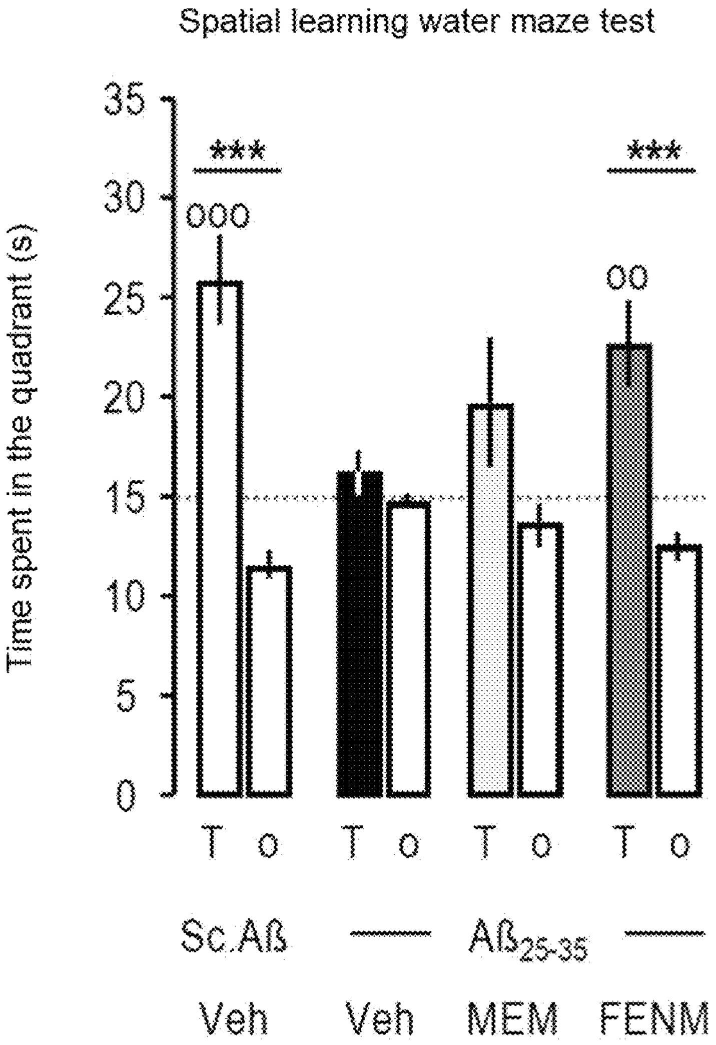

FIG. 5, neuroprotective effect of memantine (MEM) and of FENM (0.3 mg/Kg i.p.) on the impairments affecting spatial reference memory (Morris water maze) and learning induced by $A\beta_{25-35}$ oligomer intoxication. The time spent in the north-eastern quadrant, known as the training quadrant (T), or in the other quadrants (o) was analysed by video surveillance.°°° $p<0.001$ vs. 15 s; one-sample t-test; *** $p<0.001$ vs. o quadrants. Veh: vehicle solution; Sc. Aβ: control peptide.

Figure 6:
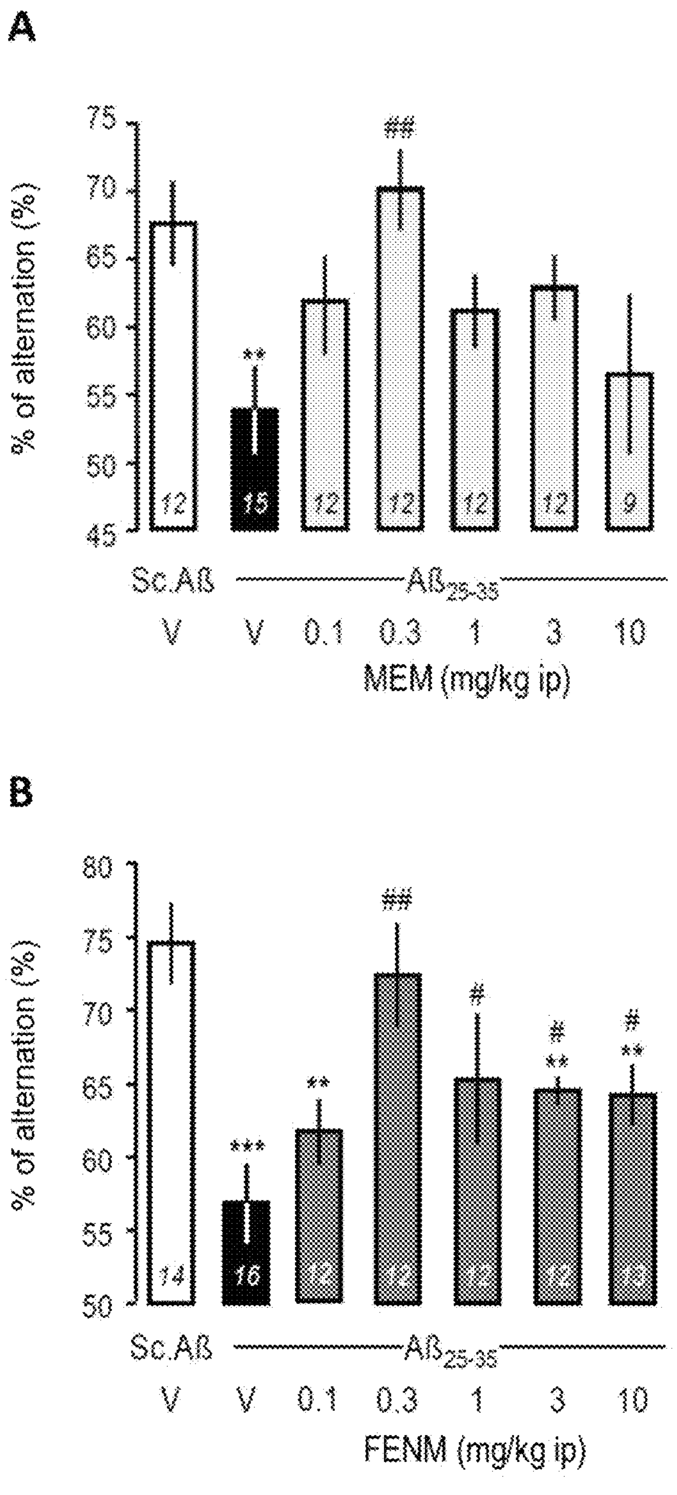

FIG. 6, symptomatic effect of memantine (A) and of FENM (B) (0.1-10 mg/Kg i.p.) on memory impairment induced by the oligomerised $A\beta_{25-35}$ peptide in the Y-maze test. ANOVA: A, $F_{(6,83)}=2.62$, $p<0.05$; B, $F_{(6,89)}=4.94$, $p<0.001$.).  $p<0.01$, * $p<0.001$ vs. (Sc. Aβ+V); #$p<0.05$, ##$p<0.01$ vs. (V+$A\beta_{25-35}$); Dunnett's test, V: vehicle solution; Sc. Aβ: control peptide. The number of mice per group is indicated in each column.

Figure 7:
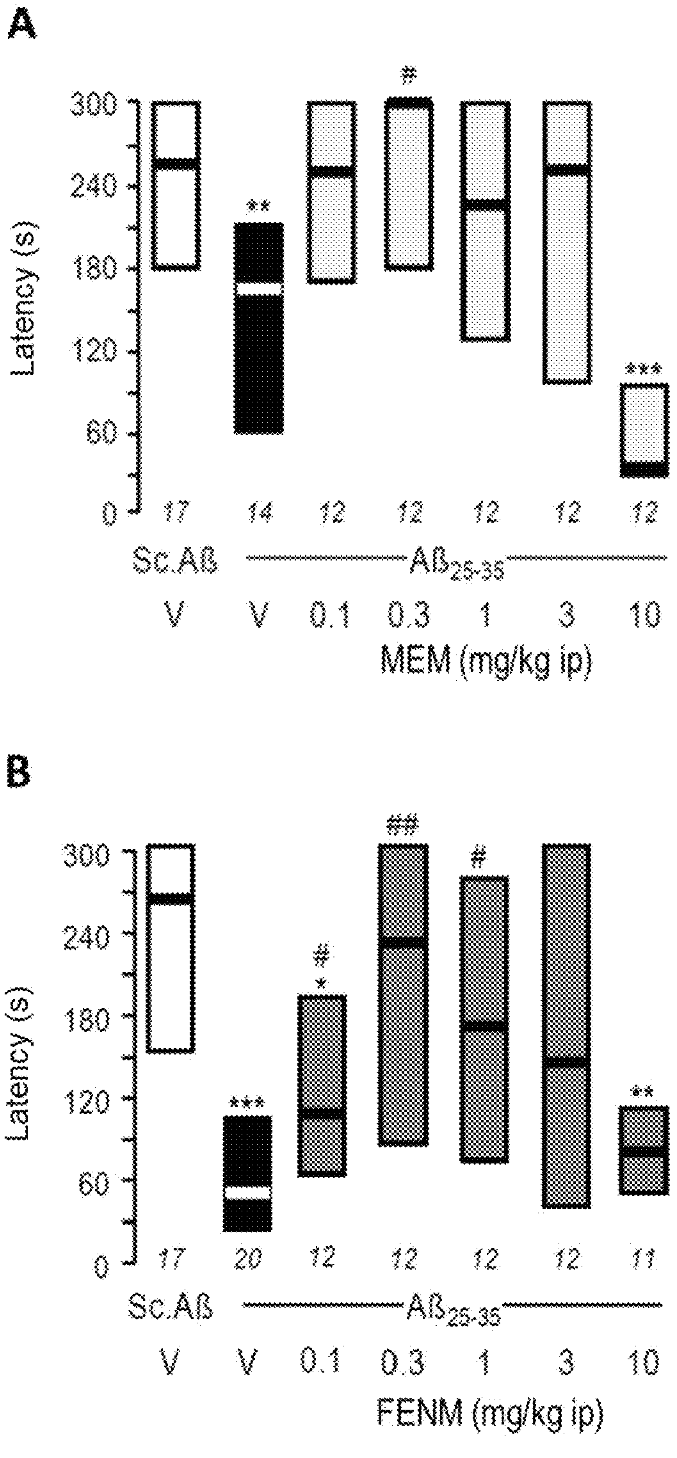

FIG. 7, symptomatic effect of memantine and of FENM (0.1-10 mg/Kg i.p.) on memory impairment induced by $A\beta_{25-35}$ oligomer intoxication in the passive avoidance test. The results are nonparametric data and are presented with the median and interquartile ranges. Kruskal-Wallis ANOVA: A, H=23.4, $p<0.001$; B, H=19.5, $p<0.01$, in (d). * $p<0.05$,  $p<0.01$, * $p<0.001$ vs. (Sc.Aβ+V); #$p<0.05$, ##$p<0.01$ vs. (V+$A\beta_{25-35}$); Dunn's test. V: vehicle solution; Sc. Aβ: control peptide. The number of mice per group is indicated in each column.

Figure 8:
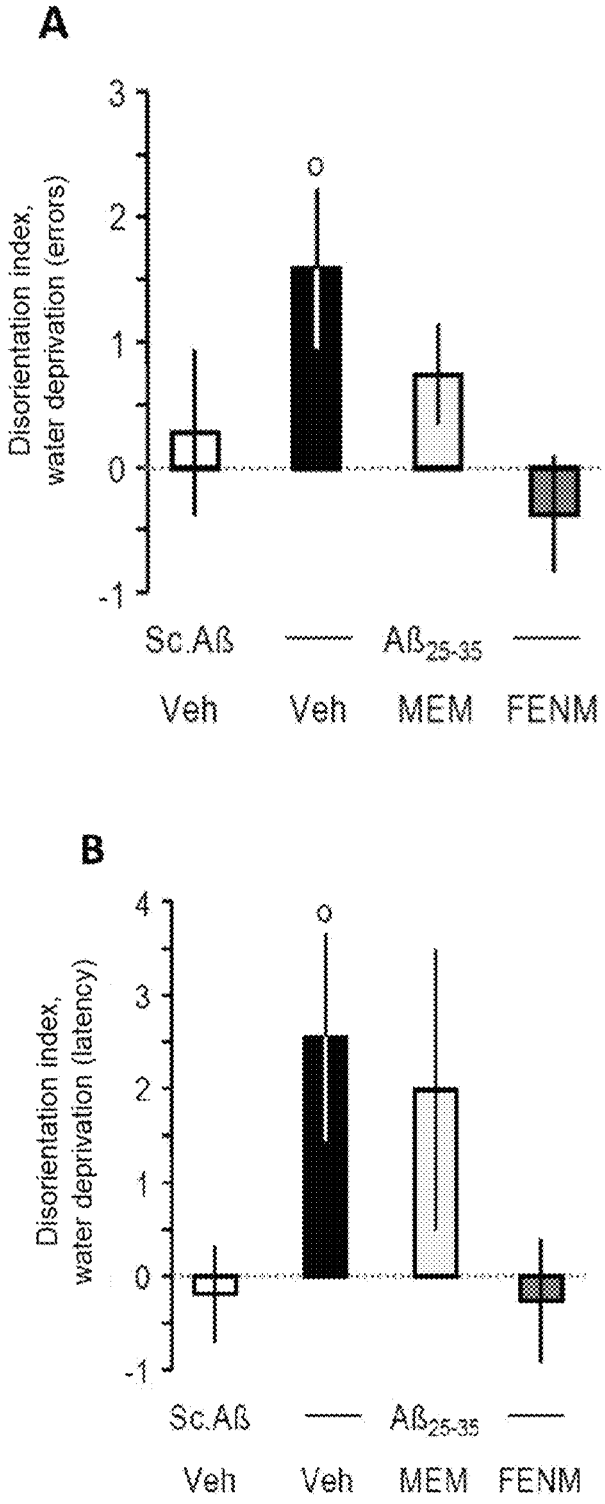

FIG. 8, symptomatic effect of memantine and of FENM (0.3 mg/Kg i.p.) on the impairment of complex memory abilities in the Hamlet Test®. The disorientation index is calculated from the errors (A) or latencies (B). $p<0.05$ vs. zero level, one-sample t-test. V: vehicle solution; Sc. Aβ: control peptide.

DESCRIPTION OF THE INVENTION

The present invention relates to 2-fluoroethyl normemantine (FENM) for use in inducing neuroprotection in a subject in need thereof. The invention further relates to combinations of FENM for use in inducing said neuroprotection.

More specifically, it has been found, as shown in the experimental part, that FENM protects neuronal cells and prevents induced cell death by decreasing apoptosis, oxidative stress in said cells and by decreasing neuroinflammation in the brain. This results in preventing the cognitive deficits produced thereby. This also leads to an efficient, symptomatic correction of the cognitive disorders induced by neurotoxicity.

Definitions

In the context of the present invention, reference to a specific drug or compound includes not only the specifically named drug or compound, but also any pharmaceutically acceptable salt, hydrate, derivative, isomer, racemate, enantiomerically pure composition, conjugate or corresponding prodrug of the active molecule of the drug or of said compound. Preferably, reference to a compound includes the specifically named compound, as well as any pharmaceutically acceptable salt, hydrate, isomer, racemate, isomer, or enantiomerically pure composition of said compound. More preferably, the designation of a compound is intended to designate the compound as specifically designated per se, as well as any pharmaceutically acceptable salt thereof.

The term "pharmaceutically acceptable salts" is understood herein to mean a pharmaceutically acceptable and relatively non-toxic inorganic or organic acid addition salt of a compound of the present invention. Pharmaceutical salt formation consists of coupling an acidic, basic or zwitterionic drug molecule with a counterion to create a saline version of the drug. A wide variety of chemical species can be used in the neutralisation reaction. The pharmaceutically acceptable salts of the invention thus include those obtained by reacting the main compound, acting as a base, with an inorganic or organic acid to form a salt, for example, salts of acetic acid, nitric acid, tartaric acid, hydrochloric acid, sulphuric acid, phosphoric acid, methanesulphonic acid, camphorsulphonic acid, oxalic acid, maleic acid, succinic acid or citric acid. Pharmaceutically acceptable salts of the invention further include those in which the main compound functions as an acid and is reacted with a suitable base to form, for example, sodium, potassium, calcium, magnesium, ammonium or choline salts. Although most salts of a given active ingredient are bioequivalent, some can have, among other things, enhanced solubility or bioavailability properties. Salt selection is now a common, standard operation in the drug development process as taught by Stahl and Wermuth in their handbook (Stahl and Wermuth).

The term "neuroprotection" is understood herein to mean the prevention or slowing of the progression of a disease affecting the central or peripheral nervous system by stopping or at least slowing the loss of functionality of nerve cells, and the degeneration or loss of cells in these systems, in particular of neurons, leading to cognitive decline. Thus, a subject in need of neuroprotection is defined as a subject suffering from, suspected of suffering from, or considered to be at risk of suffering from a pathology linked to neuronal cell death and/or neurodegeneration, in particular linked to excitotoxicity, but not limited thereto. These pathologies are, for example, neurodegenerative pathologies such as tauopathies, synucleopathies or amyloidopathies such as Alzheimer's disease, Parkinson's disease, multiple system atrophy, dementia with Lewy bodies, corticobasal degeneration, Pick's disease, frontotemporal dementia, or posterior cortical atrophy. Other neurodegenerative pathologies include, for example, Huntington's disease, amyotrophic lateral sclerosis, epilepsy, vascular dementia, Korsakoffs syndrome, or acute neuronal pathologies such as alcohol withdrawal, ischaemia, neonatal ischaemia, head injury, or stroke.

The term "subject" is understood herein to mean any member of the animal kingdom, preferably mammals and even more preferably humans. In another preferred embodiment, bees, insects that also have an NMDA system controlling memory generation, are also included.

The terms "combination", "combination treatment" or "combination therapy" are understood to mean a combination whose base is made of the compound of formula (I) or a pharmaceutically acceptable salt thereof (i.e. FENM), and at least one other compound or drug co-administered to said subject for the purpose of achieving a biological effect.

FENM and said at least one other compound in this combination can be administered together or separately, concomitantly or sequentially. When administered together, they can be administered in a single composition comprising the FENM and said at least one other compound or drug. In other words, the FENM and said at least one other compound or drug are thus formulated together. Alternatively, they can be administered separately to said subject, by the same or a different route of administration. Thus, for example, the FENM can be administered orally and said at least one other compound with which the FENM is co-administered can be injected into said subject, for example, intravenously or subcutaneously. In another embodiment, for example, the FENM can be administered orally and said at least one other compound with which the FENM is co-administered can also be administered orally to said subject. Preferably, the sequence of administration of the active ingredients of the combination is such that said active ingredients or the active metabolites exert their biological effects at the same time, such that the subject benefits from the maximum effect of said combination. Thus, in a particularly preferred manner, the FENM and said at least one other compound or drug are administered so as to reach their maximum concentration in the plasma or cerebrospinal fluid, preferably in the cerebrospinal fluid, at the same time.

"A-beta peptides", "Aβ", "beta-amyloid peptides", "amyloid peptides", or "beta-amyloid" result from the cleavage by gamma and beta secretases of the APP protein ("Amyloid Protein Precursor") located in the membrane of the neurons. In humans, they can vary in size (mainly from 38 to 42 amino acids) and are present in oligomeric assemblies of varying size and solubility. Each type of oligomer is potentially toxic, leading to alterations in synaptic structure, function and plasticity that ultimately result in neuronal death (Pike et al., 1991). This alteration of the synapses is the cause of the dysfunction of the regions involved in the memory and learning processes. These fragments are also found in the so-called amyloid plaques that accumulate with age or with certain diseases. In vivo, in humans, $A\beta_{31}$_42 has a strong propensity to self-aggregate; familial forms of Alzheimer's disease are accompanied by an increase in the relative level of $A\beta_{1-42}/A\beta_{1-40}$ peptide, and it is this relative level that would be indicative of the diagnosis of the pathology rather than the accumulation of the $A\beta_{1-42}$ and/or $A\beta_{1-40}$ peptides. $A\beta_{25-35}$ is a fragment that is toxic to neuronal cells in vitro. In mice and rats, the intracerebroventricular (icy) injection of $A\beta_{25-35}$ peptide oligomers is one of the models used to study Aβ oligomer-induced neurodegeneration, in particular in Alzheimer's disease and to test drug candidates for this disease (Maurice et al., 1996). Neurotoxicity of "A beta peptides", "Aβ", "beta-amyloid peptides", "amyloid peptides", or "beta-amyloid" is understood herein to mean the neurotoxicity induced by any oligomer and/or aggregate formed by one or more peptides resulting from the cleavage of the APP protein.

The applicants have found that FENM is effective in inducing neuroprotection against toxicity induced by the intracerebral injection of $A\beta_{25-35}$ oligomers in an animal model. $A\beta_{25-35}$ oligomers are known to induce an inflammatory process, oxidative stress and apoptosis of the neuronal cells when injected into the brain of animal models. Surprisingly, the administration of FENM to animals on the day of the $A\beta_{25-35}$ oligomer injection reduces the levels of apoptosis and mitochondrial stress markers, neuroinflammation, and reduces cell death in hippocampal cells. This reduction is accompanied by a restoration of the animals' cognitive abilities to levels that are not statistically different from those of animals not injected with $A\beta_{25-35}$. Such a level of neuroprotection is not observed for the reference NM DA receptor antagonist for neurodegenerative pathologies, memantine, which is nonetheless structurally similar. Furthermore, unlike memantine, the applicants have also observed that FENM is devoid of any amnestic effects. Finally, FENM allows for the symptomatic treatment of cognitive disorders induced by the $A\beta_{25-35}$ injection, in a more efficient way than memantine.

Thus, a first purpose of the present invention is to propose the compound of formula (I):

(I)

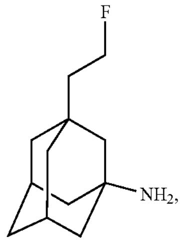

or of a pharmaceutically acceptable salt thereof, for use in inducing neuroprotection in a subject in need thereof.

In one specific embodiment, said subject in need thereof is suffering from, suspected of suffering from, or considered to be at risk of suffering from a pathology of the central nervous system. In another specific embodiment, this pathology of the central nervous system is linked to neuronal cell death and/or neurodegeneration. In another specific embodiment, this pathology of the central nervous system is linked to excitotoxicity. In another more specific embodiment, said subject is suffering from, suspected of suffering from, or considered to be at risk of suffering from a pathology of the central nervous system selected from tauopathies, synucleopathies or amyloidopathies such as Alzheimer's disease, Parkinson's disease, multiple system atrophy, dementia with Lewy bodies, cortico-basal degeneration, Pick's disease, frontotemporal dementia, posterior cortical atrophy, or pathologies such as Huntington's disease, amyotrophic lateral sclerosis, epilepsy, vascular dementia, Korsakoff's syndrome, alcohol withdrawal, ischaemia, neonatal ischaemia, head injury, or stroke.

In another specific embodiment, said subject may thus have been diagnosed with a pathology of the central nervous system. In particular, this pathology is linked to neuronal cell death and/or neurodegeneration. More particularly, said subject may have been diagnosed as suffering from a tauopathy, synucleopathy or amyloidopathy such as Alzheimer's disease, Parkinson's disease, multiple system atrophy, dementia with Lewy bodies, cortico-basal degeneration, Pick's disease, frontotemporal dementia, posterior cortical atrophy, or pathologies such as Huntington's disease, amyotrophic lateral sclerosis, epilepsy, vascular dementia, Korsakoffs syndrome, alcohol withdrawal, ischaemia, neonatal ischaemia, head injury, or stroke. This diagnosis is based on behavioural, cognitive, biological and/or medical imaging analyses well known to a person skilled in the art. In such a case, the neuroprotection procured by compound of formula (I) will allow the progression of the disease to be slowed or halted, i.e. the neuronal cell death and/or neurodegeneration already initiated in the context of the disease thus diagnosed to be slowed or halted. As a result, said neuroprotection thus procured with said subject will result in the halting, or slowing down, of the progression of the cognitive impairment resulting from neurodegeneration and of the symptoms associated therewith.

In another specific embodiment, said subject can also be suspected of suffering from a pathology linked to neuronal cell death and/or neurodegeneration. In other words, the diagnosis made for this subject is uncertain, i.e., for example, the subject does not present a level of symptoms (as regards their intensity), or all of the different symptoms or signs of the clinical picture that allow a formal diagnosis of the pathology to be made. However, in this subject, the symptoms or signs noted are relevant to the pathology. This can be, for example, patients in the early stages of the disease and who are thus only showing a few, potentially mild, precursory signs. More particularly, said subject has relevant signs or symptoms compatible with a tauopathy, synucleopathy or amyloidopathy such as Alzheimer's disease, Parkinson's disease, multiple system atrophy, dementia with Lewy bodies, cortico-basal degeneration, Pick's disease, frontotemporal dementia, posterior cortical atrophy, or relevant signs or symptoms compatible with pathologies such as Huntington's disease, amyotrophic lateral sclerosis, epilepsy, vascular dementia, Korsakoff's syndrome, alcohol withdrawal, ischaemia, neonatal ischaemia, head injury, or stroke.

The relevant signs or symptoms can be detected by behavioural, cognitive, biological and/or medical imaging analyses well known to a person skilled in the art and commonly used in the diagnosis of these pathologies.

The tests routinely used for the cognitive assessment of human subjects are, for example, the Mini-Mental State Examination (MMSE or Folstein test), the Modified Mini-Mental State Examination (or 3 MS scale), the Abbreviated Mental Test Score (AMTS), the Dementia questionnaire for persons with Mental Retardation (or DMR questionnaire), the Cognitive Abilities Screening Instrument (CASI), the Trail-making test, the Clock drawing test, the Alzheimer's disease assessment scale-Cognition (ADAS-Cog), the General Practitioner Assessment of Cognition (GPCOG), the Montreal Cognitive Assessment (MoCA), the Rowland Universal Dementia Assessment Scale (RUDAS), or the Alzheimer's Disease Cooperative Study-Activities of Daily Living (ADCS-ADL).

More particularly, the MMSE can be used to identify people with major neurocognitive impairment (dementia) without linking it to a particular pathology. The MMSE is also used to monitor a person's cognitive state and to measure the decline in cognitive function in people with neurocognitive impairment. This test assesses orientation, registration, attention and calculation, recall, language and copying skills. The CERAD (Consortium to Establish a Registry for Alzheimer's Disease) has established a dementia severity scale associated with MMSE scores. A score between 19 and 24 is associated with mild dementia, between 10 and 18 with moderate dementia, and a score below 10 with severe dementia, with a maximum score of 30.

The ADAS-Cog is a cognitive subscale of the Alzheimer's Disease Assessment Scale and thus only addresses the cognitive aspects of dementia. It can thus be used to assess (i.e. score) and monitor the progress of any type of dementia. The ADAS-Cog assesses orientation, memory, executive functioning, visuospatial abilities, language or praxis, with a range of scores from 0 to 70, a higher score indicating more severe impairment. The ADAS-Cog is considered to be more sensitive than the MMSE. It is one of the most commonly used tests for clinically evaluating candidate compounds with a view to obtaining Marketing Authorisation in the context of anti-dementia treatments as well as for measuring how cognitive impairment is progressing.

Medical imaging can be used to identify structural or functional damage to particular areas of the brain, and thus also help to diagnose some of these neurodegenerative pathologies. For example, brain scans with ioflupane can be used to characterise the damage to dopaminergic neurons in Parkinson's disease or dementia with Lewy bodies. 18F-labelled FENM is being considered as a marker for NMDA receptors by positron emission tomography (PET) and is the subject of a pilot study in humans (Beaurain et al., 2019). MRI or PET scans can be used to diagnose, for example, frontotemporal dementia (by identifying frontal and temporal lobe atrophy) or Alzheimer's disease (cortical atrophy and/or hippocampal atrophy). Thus, in one specific embodiment, the subject in need of neuroprotection has dopaminergic neuron damage, fronto and/or temporal atrophy, or cortical atrophy and/or atrophy of one or both hippocampi.

The analysis of the presence of certain proteins in the CSF can be used to diagnose, for example, Alzheimer's disease, the typical profile whereof combines a decrease in the concentration of the $A\beta_{42}$ peptide and an increase in the Tau proteins and their phosphorylated forms P-Tau. In some cases, the $A\beta_{1-40}$ dosing and the measurement of the $A\beta_{1-42}/A\beta_{1-40}$ ratio can improve the diagnosis. Imaging and CSF markers allow diseases to be diagnosed early, in some cases before the onset of cognitive symptoms. Thus, in one specific embodiment, the subject in need of neuroprotection has an abnormal profile as regards the levels of $A\beta_{1-42}$ and/or $A\beta_{1-40}$ peptides and/or Tau protein and/or its phosphorylated forms and/or the $A\beta_{1-42}/A\beta_{1-40}$ ratio.

Moreover, analysing Event-Related Potential (ERP) recordings is of great use in evaluating cognitive processes because the results are independent of the stimulus used. ERPs are observed in response to a discordant stimulus and represent activated cognitive phenomena such as perception, attention, decision making, memory processes, and language, etc. ERPs are recorded, for example, by electroencephalography (EEG) or magnetoencephalography (MEG). ERPs provide information about how the brain processes the stimulus, even when no change in behaviour is noticeable. The characteristics of the ERP can vary depending on various factors such as the relevance of the stimulus, the task being performed, damage to the nervous system or the use of drugs.

ERPs are known in the prior art as cognitive biomarkers useful for diagnosing dementia, monitoring disease progression and assessing the procognitive effect of treatments. For example, ERPs are altered in patients with Alzheimer's disease, vascular dementia or dementia associated with Parkinson's symptoms, such as dementia with Lewy bodies. In particular, ERP measurements can detect impairment in cognitive function at an early stage, in particular in the early or mild stage of Alzheimer's disease. The ERP most frequently examined in clinical practice is the P300 (or P3) wave, which is a large centro-parietal positivity that occurs with a latency of about 300 ms after the discordant stimulus. The P300 wave can be divided into two subcomponents P3a and P3b. P3a is generally considered to be linked to the degree of focal attention, whereas P3b is believed to index the working memory updating process. The amplitude of the P300 wave refers in particular to motivation (in relation to the difficulty of the task) and vigilance in relation to the probability of occurrence of the stimulus. Latency refers to the time it takes to make a decision. An increase in the latency of P300 (or its subcomponents) and a decrease in its amplitude (or that of its subcomponents) are observed in patients with dementia, in particular Alzheimer's disease. Studying changes to latency is useful for monitoring the progression of dementia, in particular of Alzheimer's disease, and for assessing the response to treatment for Alzheimer's disease.

Thus, in one specific embodiment, the subject in need of neuroprotection has impaired cognitive abilities. Preferably, this impairment is measured by the MMSE or ADAS-Cog. In a particularly preferred manner, said subject has an MMSE score of less than 30, less than or equal to 29, 28, 27, 26, 25, 24, 23, 22, 21, 20, 19, 18, 17, 16, 15, 14, 13, 12, 11, 10, 9, 8, 7, 6, 5, 4, 3, or less than or equal to 2. Equally preferably, this impairment is measured in said subject by analysing the P300 wave of the subject's ERPs, the subject exhibiting a decrease in the amplitude and/or latency of the P300 wave or a component thereof.

In another specific embodiment, said subject in need of neuroprotection has mild dementia. In another specific embodiment, said subject in need of neuroprotection has moderate dementia. In another specific embodiment, said subject in need of neuroprotection has severe dementia. In a particularly preferred manner, the subject in need of neuroprotection has mild dementia. Thus, in one specific embodiment, the invention relates to the compound of formula (I) or a pharmaceutically acceptable salt thereof, for use in inducing neuroprotection in a subject suffering from mild dementia.

In a particularly preferred manner, the subject in need of neuroprotection has been diagnosed as suffering from a pathology of the central nervous system linked to neuronal cell death and/or neurodegeneration as defined hereinabove, however does not exhibit cognitive symptoms or symptoms have not been detected in this subject. Thus, due to the neuroprotective properties described in the experimental part, the onset of these symptoms can be prevented, delayed or slowed down, and consequently the quality of life of the patients can be maintained and the onset of other pathologies associated with neurodegenerative pathologies, in particular psychiatric pathologies such as depression, can be prevented.

Finally, said subject in need of neuroprotection can also be considered to be a subject at risk of suffering from a pathology of the central nervous system, in particular a pathology linked to neuronal cell death and/or neurodegeneration as described hereinabove. In other words, said subject does not have any symptoms or signs associated with said pathology, but has an increased risk of developing this pathology compared to the general population, because he/she has risk factors linked to his/her lifestyle, genetic predispositions or family history, to the presence of co-morbidities and/or to his/her age. More particularly, said subject has a lifestyle, genetic predispositions or a family history, suffers from co-morbidities and/or has an age which increase his/her risk (compared to the general population) of developing a tauopathy, a synucleopathy or an amyloidopathy such as Alzheimer's disease, Parkinson's disease, multiple system atrophy, dementia with Lewy bodies, corticobasal degeneration, Pick's disease, frontotemporal dementia, posterior cortical atrophy, or of developing pathologies such as Huntington's disease, amyotrophic lateral sclerosis, epilepsy, vascular dementia, Korsakoffs syndrome, alcohol withdrawal, ischaemia, neonatal ischaemia, head injury, or stroke.

For example, but in a non-limiting manner, age is the primary risk factor for dementia, which includes Alzheimer's disease, since 5 to 8% of people over 60 suffer therefrom. One example of genetic predispositions to CNS diseases, a pathology which is linked to neuronal cell death and/or neurodegeneration is the presence of the ε4 allele of apolipoprotein E (ApoE), which is associated with an increased risk of several dementias, in particular Alzheimer's disease (Liu et al. 2013); additionally, for example, mutations in the SNCA (alpha-synuclein), PRKN (parkin), LRRK2 (leucine-rich repeat kinase 2), PINK1 (PTEN-induced putative kinase 1), DJ-1 and ATP13A2 genes and in the 11 loci of the PARK1-PARK11 genes are associated with an increased risk of Parkinson's disease for the carrier of such genetic predispositions or mutations; the SOD1 gene mutation and its link to amyotrophic lateral sclerosis or mutations in the gene encoding huntingtin are also examples of genetic predisposition to CNS diseases. Co-morbidities associated with an increased risk of developing these pathologies include, for example, Down's syndrome, post-traumatic stress disorder (PTSD), depression, high blood pressure, diabetes, head injury or stroke. Excessive alcohol consumption is associated with an increased risk of dementia. Exposure to certain metals such as manganese, copper, lead or to certain chemical compounds such as paraquat, rotenone or maneb is associated with an increased risk of developing Parkinson's disease.

Thus, in one embodiment, the subject in need of neuroprotection is a subject with a risk factor for a pathology of the central nervous system, more particularly a pathology linked to neuronal cell death and/or neurodegeneration. More particularly, the subject has no other symptoms of the pathology. Preferably, the subject has no cognitive symptoms of the pathology. In a preferred embodiment, the subject has a genetic predisposition to said pathology. In another preferred embodiment, the subject has a pathology associated with an increased risk of developing a pathology of the central nervous system, more particularly a pathology linked to neuronal cell death and/or neurodegeneration. The administration of the compounds of formula (I) in these subjects defined as at risk and in need of neuroprotection allows the onset of these pathologies and/or the symptoms thereof, in particular a pathology of the central nervous system, more particularly a pathology linked to neuronal cell death and/or neurodegeneration, to be prevented or delayed.

In another specific embodiment, the present invention relates to the compound of formula (I) or a pharmaceutically acceptable salt thereof, for use in inducing neuroprotection in a subject suffering from PTSD. Another specific embodiment of the present invention relates to the compound of formula (I) or a pharmaceutically acceptable salt thereof, for inducing neuroprotection in a subject suffering from PTSD, for example to prevent the onset of Alzheimer's disease or its symptoms.

The experimental data presented show that the compound of formula (I) is particularly effective in preventing neuroinflammation, oxidative stress and apoptosis of the neuronal cells induced by Aβ-oligomer toxicity and which are the source of neurodegeneration and CNS cell death, more particularly neuronal death, in many pathologies, such as, but not limited to, Alzheimer's disease.

Thus, one purpose of the present invention is also to propose the compound of formula (I) or a pharmaceutically acceptable salt thereof for use in preventing or decreasing the toxicity of Aβ oligomers, and more particularly in preventing or decreasing the neurotoxicity of Aβ oligomers. One specific embodiment of the invention further relates to the compound of formula (I) or a pharmaceutically acceptable salt thereof for use in preventing or decreasing the toxicity of Aβ oligomers, and more particularly in preventing or decreasing the neurotoxicity of Aβ oligomers, in a subject suffering from, suspected of suffering from, or at risk of suffering from Alzheimer's disease or a pathology in which Aβ aggregates or oligomers are implicated, such as dementia with Lewy bodies.

As mentioned hereinabove, neuroinflammation, oxidative stress and apoptosis of neuronal cells are observed in many neurodegenerative pathologies.

Another purpose of the present invention is also to propose the compound of formula (I) or a pharmaceutically acceptable salt thereof for use in preventing or decreasing neuroinflammation in a subject in need thereof. One purpose of the present invention is also to propose the compound of formula (I) or a pharmaceutically acceptable salt thereof for use in preventing or decreasing oxidative stress in a subject in need thereof. One purpose of the present invention is also to propose the compound of formula (I) or a pharmaceutically acceptable salt thereof for use in preventing or decreasing apoptosis in the CNS in a subject in need thereof, comprising administering to said subject a compound of formula (I) or a pharmaceutically acceptable salt thereof. One purpose of the present invention is also to propose the compound of formula (I) or a pharmaceutically acceptable salt thereof for use in preventing or decreasing hippocampal cell loss in said subject. This loss can be detected, as mentioned hereinabove, for example, by the observation of atrophy, of a decrease in volume, of a change in the shape of the hippocampus or of atrophy or a decrease in the cerebral cortex, for example by Magnetic Resonance Imaging (MRI). In one specific embodiment, the compounds and combinations for use according to the invention comprise structural and/or functional monitoring of the CNS by medical imaging.

In one specific embodiment of each of these purposes, said subject suffers from, is suspected of suffering from, or is considered to be at risk of suffering from a pathology of the central nervous system selected from tauopathies, synucleinopathies, amyloidopathies, Alzheimer's disease, Parkinson's disease, multiple system atrophy, Huntington's disease, posterior cortical atrophy, Pick's disease, epilepsy, vascular dementia, frontotemporal dementia, dementia with Lewy bodies, amyotrophic lateral sclerosis, Korsakoffs syndrome, alcohol withdrawal, ischaemia, neonatal ischaemia, head injury, or stroke, preferably Alzheimer's disease.

In relation to the prevention of cellular and biochemical mechanisms underlying neurodegeneration and CNS cell death, more particularly neuronal cell death, the compound of formula (I) has been found to be particularly effective in the prevention and symptomatic treatment of cognitive impairment in an animal neurodegeneration and dementia model. Experimental data show that the compound of formula (I) is effective, under pathological conditions, in maintaining and protecting many different types of memory and cognitive processes that involve various neuronal mechanisms and brain areas.

Thus, one purpose of the present invention is also to propose the compound of formula (I) or a pharmaceutically acceptable salt thereof for use in preventing or decreasing cognitive impairment in a subject in need thereof. "Cognitive abilities" must be understood herein to mean intellectual functions such as memory, perception, coordination and reasoning. The ADAS-Cog, in particular, is a composite test that allows these different aspects of cognition to be tested in subjects. Another specific purpose of the invention is to propose the compound of formula (I) or a pharmaceutically acceptable salt thereof for use in preventing or decreasing short-, intermediate- and/or long-term memory impairment in a subject in need thereof. Another specific purpose of the invention is to propose the compound of formula (I) or a pharmaceutically acceptable salt thereof for use in preventing or decreasing spatial memory impairment in a subject in need thereof, comprising administering to said subject a compound of formula (I) or a pharmaceutically acceptable salt thereof. Another specific purpose of the invention is to propose the compound of formula (I) or a pharmaceutically acceptable salt thereof for use in preventing or decreasing impairments in recognition and/or learning abilities in a subject in need thereof. In one specific embodiment of each of these purposes, said subject suffers from, is suspected of suffering from, or is considered to be at risk of suffering from a pathology of the central nervous system selected from tauopathies, synucleinopathies, amyloidopathies, Alzheimer's disease, Parkinson's disease, multiple system atrophy, Huntington's disease, posterior cortical atrophy, Pick's disease, epilepsy, vascular dementia, frontotemporal dementia, dementia with Lewy bodies, amyotrophic lateral sclerosis, Korsakoff's syndrome, alcohol withdrawal, ischaemia, neonatal ischaemia, head injury, or stroke, preferably Alzheimer's disease.

The MMSE and/or ADAS-Cog can be used to easily monitor the progression of symptoms and thus monitor the neuroprotection procured by the compound of formula (I) or a pharmaceutically acceptable salt or combination thereof for use according to the invention. A decrease in the MMSE score or an increase in the ADAS-cog (or one of the items thereof) is indicative of a deterioration in the cognitive abilities of the individual tested. In a non-limiting manner, it has been estimated that the average deterioration in cognitive performance in the mild and moderate stages of the disease represents the loss of 2 to 4 points per year on the MMSE and an increase of 6 to 8 points per year on the ADAS-Cog (Alzheimer's Disease Institute; <http://www.i-maalzheimer.com>. ADAS-Cog). An increase in the ADS-cog on two consecutive tests will indicate a worsening of the disease and/or symptoms. A decrease in the MMSE on two consecutive tests will indicate a worsening of the disease and/or symptoms. Tests can be conducted every 1, 2, 3, 4 weeks, every month, every 2, 3, 4, 5, 6, 7, 8, 9, 10, 11, 12 months or 3 to 4 times a year or even once a year. For example, an increase of less than or equal to 20%, 15%, preferably less than or equal to 10%, or even preferably less than or equal to 5% in the Adas-Cog for two tests conducted one month apart will indicate neuroprotection. For example, a decrease of less than or equal to 20%, 15%, preferably less than or equal to 10%, or even preferably less than or equal to 5% in the MMSE for two tests conducted one month apart will indicate neuroprotection. Alternatively, a slowing of the worsening of the cognitive symptoms compared to the usual course of the pathology will indicate neuroprotection. Moreover, a slowing of the deterioration of the score for one or more categories of memory or cognitive performance as measured in the composite scores, but not necessarily of the overall test score, will indicate neuroprotection. In one specific embodiment, the compounds and combinations for use according to the invention comprise monitoring the subject's cognitive state during treatment, preferably by application of an MMSE or ADAS-Cog test.

As mentioned hereinabove, analysing the ERPs allows the progression of the symptoms of neurodegeneration to be monitored, and thus can be used to monitor the neuroprotection procured by the compound of formula (I) or a pharmaceutically acceptable salt or combination thereof for use according to the invention. An increase in latency in the occurrence of the P300 wave and/or a decrease in the amplitude thereof is indicative of a deterioration in the cognitive abilities of the individual tested. Thus, a decrease in the latency of the P300 wave and/or an increase in the amplitude thereof will indicate neuroprotection. In one specific embodiment, the compounds and combinations for use according to the invention comprise monitoring the subject's cognitive state during treatment, preferably by analysing the ERPs by EEG or MEG.

Another purpose of the invention is to propose the compound of formula (I) or a pharmaceutically acceptable salt thereof for use in preventing or treating a pathology of the central nervous system selected from tauopathies, synucleopathies or amyloidopathies such as Alzheimer's disease, Parkinson's disease, multiple system atrophy, dementia with Lewy bodies, cortico-basal degeneration, Pick's disease, frontotemporal dementia, posterior cortical atrophy, or pathologies such as Huntington's disease, amyotrophic lateral sclerosis, epilepsy, vascular dementia, Korsakoff's syndrome, alcohol withdrawal, ischaemia, neonatal ischaemia, head injury, or stroke, preferably Alzheimer's disease, in a subject in need thereof. One specific purpose of the invention is to propose the compound of formula (I) or a pharmaceutically acceptable salt thereof for use in preventing or treating Alzheimer's disease in a subject in need thereof. The person can have mild (also called early-onset), moderate or advanced Alzheimer's disease. In a preferred embodiment, said subject suffers from mild Alzheimer's disease.

Another purpose of the invention is to propose the compound of formula (I) or a pharmaceutically acceptable salt thereof for use in preventing or treating dementia in a subject in need thereof. In one specific embodiment, the subject suffers from mild dementia (e.g. cognitive decline).

Another purpose of the invention is to propose the compound of formula (I) or a pharmaceutically acceptable salt thereof for use in preventing or treating excitotoxicity in a subject suffering from, suspected of suffering from or considered to be at risk of suffering from a pathology of the central nervous system selected from tauopathies, synucleopathies or amyloidopathies such as Alzheimer's disease, Parkinson's disease, multiple system atrophy, dementia with Lewy bodies, cortico-basal degeneration, Pick's disease, frontotemporal dementia, posterior cortical atrophy, or pathologies such as Huntington's disease, amyotrophic lateral sclerosis, epilepsy, vascular dementia, Korsakoff's syndrome, alcohol withdrawal, ischaemia, neonatal ischaemia, head injury, or stroke, preferably Alzheimer's disease. One specific purpose of the invention is to propose the compound of formula (I) or a pharmaceutically acceptable salt thereof for use in preventing or treating excitotoxicity in a subject suffering from Alzheimer's disease in a subject in need thereof.

In one specific embodiment, a pharmaceutically acceptable salt of the compound of formula (i) is selected from the salts of formula (II):

(II)

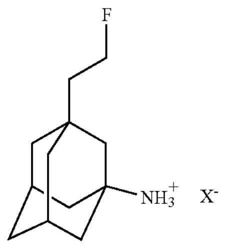

wherein $X^-$ denotes a counteranion selected from the group consisting of chloride, bromide, iodide, acetate, methane sulphonate, benzene sulphonate, camphosulphonate, tartrate, dibenzoate, ascorbate, fumarate, citrate, phosphate, salicylate, oxalate, bromohydrate, and tosylate ions. Preferably, the counteranion is the chloride ion.

Without wishing to be bound by any scientific theory, this action of FENM can be believed to be linked to its NM DA receptor antagonist effect and thus its excitotoxicity modulation effect. Although structurally similar to memantine, this compound differs therefrom with unexpected properties, since it induces significant neuroprotection which memantine does not. Furthermore, FENM does not have the harmful effects on memory that memantine does when administered in large doses, which is of particular benefit, in particular in the case of neurodegenerative pathologies that result in dementia and/or cognitive disorders in affected subjects. Large doses of this compound can thus be administered to the subject to achieve effective doses in the central nervous system, which was not possible with memantine, for which the maximum authorised dose (20 mg per day for Ebixa®) does not allow the $IC_{50}$ value for NMDA receptors in cerebrospinal fluid (CSF) to be reached. Finally, FENM seems to have a totally different, unexpected and much more favourable dose-effect curve than memantine. FENM is active in animals over a significantly wider dose range compared to memantine. These unexpected properties allow much larger useful dose ranges to be considered compared to memantine, thus facilitating galenic formulation and obtaining a treatment that is more effective than memantine.

In one specific embodiment, the compound of formula (I), or a pharmaceutically acceptable salt thereof or the compound of formula (II) for use in a subject in need thereof, has, at the dose administered, no adverse cognitive effects, in particular amnestic effects, on the patient.

Preferably, the compound of formula (I), or a pharmaceutically acceptable salt thereof or the compound of formula (II) is administered to the subject as a pharmaceutical preparation, for example, but not limited to, orally or parenterally (subcutaneously or intravenously). Oral administration is particularly preferred.

In one embodiment, the compound of formula (I), or a pharmaceutically acceptable salt thereof or the compound of formula (II) is administered to the subject at an oral dose of between 1 and 1,000 mg per day inclusive, preferably between 5 and 500 mg per day, more preferably between 10 and 100 mg per day, particularly preferably between 20 and 70 mg per day, even more preferably between 30 and 60 mg per day.

In another embodiment, the compound of formula (I), or a pharmaceutically acceptable salt thereof, or the compound of formula (II), is administered at an oral dose of greater than 20 mg per day, preferably greater than or equal to 30 mg per day, 40 mg, 50 mg, 60 mg, 70 mg, 80 mg, 90 mg, or even greater than or equal to 100 mg per day.

With regard to procuring neuroprotection in cases of chronic disease such as pathologies of the central nervous system selected from tauopathies, synucleopathies or amyloidopathies such as Alzheimer's disease, Parkinson's disease, multiple system atrophy, dementia with Lewy bodies, cortico-basal degeneration, Pick's disease, frontotemporal dementia, posterior cortical atrophy, or pathologies such as Huntington's disease, amyotrophic lateral sclerosis, epilepsy, vascular dementia, or Korsakoff's syndrome, it is readily understood that the treatment of the subject with the compound of formula (I) or with a pharmaceutically acceptable salt thereof or with the compound of formula (II), lasts for the whole life of the subject, at least for as long as the treatment has an effect. For acute pathologies such as alcohol withdrawal, ischaemia, neonatal ischaemia, head injury, or stroke, the treatment can be considered such that it is limited in time. It can last 1, 2, 3, 4, 5, 6, 7 days, or 1, 2, 3, 4, weeks, or 2, 3, 4, 5, 6, 7, 8, 9, 10, 11, 12 months, or 1, 2, 3, 4, 5, 6 years or even longer, i.e. for as long as there is a need for neuroprotection, in particular against neurotoxicity. For these acute pathologies, the treatment comprising the compound of formula (I) or (II) should be implemented as early as possible, in order to best prevent neurodegeneration, for example, on the day of their occurrence, the following day, or even the day after that.

Said doses can be unitary, i.e. administered to the subject in a single dose. The dose can also be administered via several intakes spread over the day, the number of doses in a day allowing the desired daily dose to be obtained. Thus, in one specific embodiment, the doses in question can be administered in one to four daily intakes, for example once, for example twice, for example 3 times, or even 4 times.

In one specific embodiment, the compound of formula (I) or a pharmaceutically acceptable salt thereof or the compound of formula (II) is packaged so as to provide the dose corresponding to one intake without the need for any handling operation such as a volume measurement, weighing or splitting of a tablet, which is particularly advantageous in cognitively-impaired subjects as it avoids any special handling or calculation.

In one embodiment, the compound of formula (I) or a pharmaceutically acceptable salt thereof or the compound of formula (II) is in tablet or pill form. In one specific embodiment, said tablet or pill can be divided into 1, 2, 3 or even 4 pieces so as to be able to provide the subject with the dose required for one intake using 1, 2 or 3 pieces of said tablet. This is of particular interest, for example, in cases where the treatment requires a period of dose escalation to reach the target daily dose, where the pieces can correspond to the increments and the whole tablet or pill to the target dose of the treatment.

In one specific embodiment, the treatment comprising the administration of the compound of formula (I) or a pharmaceutically acceptable salt thereof or the compound of formula (II) comprises a period of dose escalation, to allow the subject to become accustomed to the treatment. This period takes place at the start of treatment or when treatment is resumed after it has been interrupted. During this period, the daily doses are regularly increased until the maximum dose tolerated by the patient or prescribed by the practitioner is reached. For example, the dose escalation increments can be 2, 3, 4, 5, 6, 7 or more days, preferably the escalation increments are 7 days, and the doses can be increased by 5 mg per increment, or by 10 mg or more, preferably by 5 mg. Thus, in one specific embodiment, the doses are increased by 5 mg from week to week until the maximum dose tolerated by the subject or the dose prescribed by the practitioner is reached. In another embodiment, the doses are increased by 10 mg from week to week until the maximum dose tolerated by the subject or the dose prescribed by the practitioner is reached.

In another embodiment, the compound of formula (I) or a pharmaceutically acceptable salt thereof or the compound of formula (II) is formulated in liquid form. It can then be packaged as a unit dose in containers such as ampoules, or in a container such as a bottle associated with a device allowing the volume needed to obtain the adequate dose to be withdrawn and optionally administered.

Although FENM is effective when used alone to induce neuroprotection in a subject in need thereof, it can be of interest to combine it with at least one other compound known to be equally beneficial in neuroprotection or the symptomatic treatment of neurodegenerative pathologies. More specifically, these are complex diseases involving many different biochemical pathways and cellular mechanisms, which it is relevant to target, in certain instances, by a pleiotropic effect via combinations to obtain a greater therapeutic efficacy and/or to allow the dosages and/or adverse effects to be reduced.

Acetylcholinesterase inhibitors are molecule that have been authorised for more than 20 years for the symptomatic treatment of Alzheimer's disease, dementia associated with Parkinson's disease or other neurodegenerative dementias. By slowing/inhibiting the degradation of acetylcholine released from intact cholinergic neurons, these inhibitors are thought to facilitate cholinergic neurotransmission and thus have a favourable effect on cognitive deficits dependent on these cholinergic pathways during Alzheimer's disease, or dementia associated with Parkinson's disease. The acetylcholinesterase inhibitors used are donepezil, rivastigmine, and galantamine. Tacrine is less ideal, in particular because of its hepatotoxicity.

One purpose of the present invention is thus to propose a combination comprising a compound of formula (I) or a pharmaceutically acceptable salt thereof or the compound of formula (II) and at least one acetylcholinesterase inhibitor, preferably selected from donepezil, rivastigmine, galantamine or a pharmaceutically acceptable salt thereof, for use in inducing neuroprotection in a subject in need thereof. In one specific embodiment, said subject is suffering from, suspected of suffering from, or at risk of suffering from Alzheimer's disease.

Connexin modulators, more specifically mefloquine, are being tested in a clinical trial for the symptomatic treatment of Alzheimer's disease. The focus of the trial is a combination treatment of donepezil with mefloquine. Mefloquine was found to have a modulating effect on connexins and in particular connexin 43, involved in astrocyte gap junctions. Astrocytes play a role in supporting neurons in the CNS but also in information transfer and neuronal activity via tripartite synapses. A synergistic effect between donepezil and mefloquine has been reported, allowing donepezil to be administered at a lower dose with a faster effect.

One purpose of the present invention is thus to propose a combination comprising a compound of formula (I) or a pharmaceutically acceptable salt thereof or the compound of formula (II) and at least one connexin modulator inhibitor for use in inducing neuroprotection in a subject in need thereof. The connexin modulators listed in the WO 2013/064579 or WO 2010/029131 applications are incorporated herein for reference. Thus, one specific purpose of the present invention is thus to propose a combination comprising a compound of formula (I) or a pharmaceutically acceptable salt thereof or the compound of formula (II) and at least one connexin modulator such as those listed in the WO 2013/064579 or WO 2010/029131 applications. In a preferred embodiment, said at least one connexin modulator is selected from meclofenamic acid, enoxolone, mefloquine and 2-amino ethoxy diphenyl borate (APB), or a pharmaceutically acceptable salt thereof. Even more preferably, said connexin modulator is meclofenamic acid. In one specific embodiment, said subject is suffering from, suspected of suffering from, or at risk of suffering from Alzheimer's disease.

One specific purpose of the present invention is also to propose a combination comprising a compound of formula (I) or a pharmaceutically acceptable salt thereof, or of formula (II), at least one connexin modulator such as those listed in the WO 2013/064579 or WO 2010/029131 applications and at least one acetylcholinesterase inhibitor, for use in inducing neuroprotection in a subject in need thereof. In a preferred embodiment, said at least one connexin modulator is selected from meclofenamic acid, enoxolone, mefloquine and 2-amino ethoxy diphenyl borate (APB), or a pharmaceutically acceptable salt thereof. Even more preferably, said connexin modulator is meclofenamic acid. In a preferred embodiment, said at least one acetylcholinesterase inhibitor is selected from donepezil, rivastigmine and galantamine. In a more preferred embodiment, said at least one acetylcholinesterase inhibitor is donepezil. In a particularly preferred embodiment, said combination for use in inducing neuroprotection in a subject in need thereof comprises a compound of formula (I) or a pharmaceutically acceptable salt thereof or the compound of formula (II), meclofenamic acid or a pharmaceutically acceptable salt thereof and donepezil or a pharmaceutically acceptable salt thereof. In one specific embodiment, said subject is suffering from, suspected of suffering from, or at risk of suffering from Alzheimer's disease.

Despite the failures in clinical trials of several monoclonal antibody-based therapies aimed at reducing amyloid plaque formation or preventing or decreasing hyperphosphorylation of the Tau protein, this strategy remains an active avenue in the search for a treatment for Alzheimer's disease. Aducanumab is a recombinant human antibody that shows excellent selectivity for soluble and insoluble oligomeric fibrillar aggregates of Aβ, compared to non-pathogenic Aβ monomers (Arndt et al., 2018). It is currently being tested in clinical trials for the treatment of Alzheimer's disease.

One purpose of the present invention is thus to propose a combination comprising a compound of formula (I) or a pharmaceutically acceptable salt thereof or the compound of formula (II) and an antibody-based therapy for disrupting amyloid plaque formation, or preventing or decreasing hyperphosphorylation of the Tau protein. One specific purpose of the invention is to propose a combination comprising a compound of formula (I) or a pharmaceutically acceptable salt thereof or the compound of formula (II) and aducanumab or an antigen-binding fragment thereof capable of fighting against the toxicity of β-amyloid aggregates, fragments or oligomers thereof for use in inducing neuroprotection in a subject in need thereof. In one specific embodiment, said subject is suffering from, suspected of suffering from, or at risk of suffering from Alzheimer's disease or dementia with Lewy bodies.

$\sigma_1$-receptor agonists are currently being developed for several neurodegenerative indications. Neuroprotective effects procured by $\sigma_1$-receptor agonists have been observed in certain models of Alzheimer's disease but also in other pathologies such as Parkinson's disease, Huntington's disease and amyotrophic lateral sclerosis. Some of these agonists have been shown to have neuroprotective effects (Meunier et al., 2006; Maurice et al., 2019). Families of $\sigma_1$-receptor agonist and neuroprotective compounds are presented in the WO 2017/191034 application. The compounds in this application are incorporated here for reference. Additionally, PRE-084 (2-morpholin-4-ylethyl 1-phenylcyclohexane-1-carboxylate), (+)-pentazocine), (+)-SKF10,047 (1,13-dimethyl-10-prop-2-enyl-10-azatricyclo [7.3.1.0$^{2,7}$]trideca-2(7),3,5-trien-4-ol), SA4503 (1-[2-(3,4-dimethoxyphenyl)ethyl]-4-(3-phenylpropyl)piperazine), 1-(2,2-Diphenyltetrahydro-3-furanyl)-N,N-dimethylmethanamine, fluvoxamine (2-{[(E)-{5-Methoxy-1-[4-(trifluoromethyl)phenyl]pentylidene}amino]oxy}ethanamine), 4-IBP (N-(1-benzylpiperidin-4-yl)-4-iodobenzamide), igmesine ((5E)-N-(cyclopropylmethyl)-N-methyl-3,6-diphenyl-5-hexen-3-amine), OPC-14523 (1-{3-[4-(3-chlorophenyl)-1-piperazinyl]propyl}-5-methoxy-3,4-dihydro-2(1H)-quinolinone), BD-737 ((1S,2R)—N-[2-(3,4-dichlorophenyl)ethyl]-N-methyl-2-(1-pyrrolidinyl) cyclohexanamine), BHDP (6-[(4-benzylpiperazin-1-yl) methyl]-2,3-dimethoxyphenol, pridopidine (4-(3-(methylsulfonyl)phenyl)-1-propylpiperidine) are known as other $\sigma_1$-receptor agonists.

Thus, one purpose of the present invention is thus to propose a combination comprising a compound of formula (I) or a pharmaceutically acceptable salt thereof or the compound of formula (II) and at least one $\sigma_1$-receptor agonist such as those listed in the WO 2017191034 application, or selected from PRE-084 (2-morpholin-4-ylethyl 1-phenylcyclohexane-1-carboxylate), (+)-pentazocine, (+)-SKF10,047 (1,13-dimethyl-10-prop-2-enyl-10-azatricyclo [7.3.1.0$^{2,7}$]trideca-2(7),3,5-trien-4-ol), SA4503 (1-[2-(3,4-dimethoxyphenyl)ethyl]-4-(3-phenylpropyl)piperazine), 1-(2,2-diphenyltetrahydro-3-furanyl)-N,N-dimethylmethanamine, fluvoxamine (2-{[(E)-{5-methoxy-1-[4-(trifluoromethyl)phenyl]pentylidene}amino]oxy}ethanamine), 4-IBP (N-(1-benzylpiperidin-4-yl)-4-iodobenzamide), igmesine ((5E)-N-(Cyclopropylmethyl)-N-methyl-3,6-diphenyl-5-hexen-3-amine), OPC-14523 (1-{3-[4-(3-Chlorophenyl)-1-piperazinyl]propyl}-5-methoxy-3,4-dihydro-2(1H)-quinolinone), BD-737 ((1S,2R)-N-[2-(3,4-dichlorophenyl)ethyl]-N-methyl-2-(1-pyrrolidinyl) cyclohexanamine), BHDP (6-[(4-benzylpiperazin-1-yl) methyl]-2,3-dimethoxyphenol), pridopidine (4-(3-(methylsulfonyl)phenyl)-1-propylpiperidine) or a pharmaceutically acceptable salt thereof, for use in inducing neuroprotection in a subject in need thereof. In one specific embodiment, said at least one $\sigma_1$-receptor agonist is selected from 2-(2-chlorophenyl)-2-oxo-3,3,5,5-tetramethyl-[1,4,2]-oxazaphosphinane; 2-(4-chlorophenyl)-2-oxo-3,3,5,5-tetramethyl-[1,4,2]-oxazaphosphinane; 2-(3,5-dichlorophenyl)-2-oxo-3,3,5,5-tetramethyl-[1,4,2]-oxazaphosphinane; 2-(2,3-dichlorophenyl)-2-oxo-3,3,5,5-tetramethyl-[1,4,2]-oxazaphosphinane; 2-(3-fluorophenyl)-2-oxo-3,3,5,5-tetramethyl-[1,4,2]-oxazaphosphinane; 2-(4-Fluorophenyl)-2-oxo-3,3,5,5-tetramethyl-[1,4,2]-oxazaphosphinane; 2-(3-nitrophenyl)-2-oxo-3,3,5,5-tetramethyl-[1,4,2]-oxazaphosphinane; 2-(4-benzyloxycarbamoylphenyl)-2-oxo-3,3,5,5-tetramethyl-[1,4,2]-oxazaphosphinane; 2-(Pyridin-2-yl)-2-oxo-3,3,5,5-tetramethyl-[1,4,2]-oxazaphosphinane; 2-(pyridin-3-yl)-2-oxo-3,3,5,5-tetramethyl[1,4,2]-oxazaphosphinane; 2-(pyridin-4-yl)-2-oxo-3,3,5,5-tetramethyl[1,4,2]-oxazaphosphinane; 2-(pyrimidin-2-yl)-2-oxo-3,3,5,5-tetramethyl-[1,4,2]-oxazaphosphinane; 2-(Pyrimidin-5-yl)-2-oxo-3,3,5,5-tetramethyl-[1,4,2]-oxazaphosphinane; 2-(3-aminophenyl)-2-oxo-3,3,5,5-tetramethyl-[1,4,2]-oxazaphosphinane; 2-(4-aminophenyl)-2-oxo-3,3,5,5-tetramethyl-[1,4,2]-oxazaphosphinane; 2-(3-chlorophenyl)-N-methyl-2-oxo-3,3,5,5-tetramethyl-[1,4,2]-oxazaphosphinane; 2-(3-chlorophenyl)-2-thiono-3,3,5,5-tetramethyl-[1,4,2]-oxazaphosphinane; 2-(3-chlorophenyl)-2-oxo-3,3,5,5-tetramethyl-[1,4,2]-oxazaphosphinane, PRE-084 (2-morpholin-4-ylethyl 1-phenylcyclohexane-1-carboxylate), (+)-pentazocine, (+)-SKF10,047 (1,13-dimethyl-10-prop-2-enyl-10-azatricyclo[7.3.1.0$^{2,7}$]trideca-2(7),3,5-trien-4-ol), SA4503 (1-[2-(3,4-dimethoxyphenyl) ethyl]-4-(3-phenylpropyl)piperazine), 1-(2,2- diphenyltetrahydro-3-furanyl)-N,N-dimethylmethanamine, fluvoxamine (2-{[(E)-{5-Methoxy-1-[4-(trifluoromethyl) phenyl]pentylidene}amino]oxy}ethanamine) 4-IBP (N-(1-benzylpiperidin-4-yl)-4-iodobenzamide), igmesine ((5E)-N-(cyclopropylmethyl)-N-methyl-3,6-diphenyl-5-hexen-3-amine), OPC-14523 (1-{3-[4-(3-chlorophenyl)-1-piperazinyl]propyl}-5-methoxy-3,4-dihydro-2(1H)-quinolinone), BD-737 ((1S,2R)—N-[2-(3,4-dichlorophenyl) ethyl]-N-methyl-2-(1-pyrrolidinyl)cyclohexanamine), BHDP (6-[(4-benzylpiperazin-1-yl)methyl]-2,3-dimethoxy-phenol), pridopidine (4-(3-(methylsulfonyl)phenyl)-1-propylpiperidine) or a pharmaceutically acceptable salt thereof, preferably 2-(3-chlorophenyl)-2-oxo-3,3,5,5-tetramethyl-[1,4,2]-oxazaphosphinane, or a pharmaceutically acceptable salt thereof. PRE-084 (2-morpholin-4-ylethyl 1-phenylcyclohexane-1-carboxylate) or a pharmaceutically acceptable salt thereof is also preferred. In one specific embodiment, said at least one $\sigma_1$-receptor agonist is in an enantiomerically pure form. In a preferred embodiment, said at least one $\sigma_1$-receptor agonist is in the form of a racemic mixture. In one specific embodiment, said subject is suffering from, suspected of suffering from, or at risk of suffering from Alzheimer's disease.

For each of the combinations according to the invention, each of the compounds is adapted for simultaneous, separate or staggered administration as defined hereinabove, depending on the specificities of these compounds, but also preferably in such a way that these compounds or the active metabolites thereof exert their biological effects at the same time, such that the subject benefits from the maximum effect of said combination.

One purpose of the present invention is also to propose a pharmaceutical composition comprising at least one compound of formula (I) or a pharmaceutically acceptable salt thereof or the compound of formula (II) alone or in combination with another active ingredient, said composition being particularly suitable for procuring neuroprotection according to the various embodiments mentioned.

Examples

Abbreviations

- $A\beta_{25-35}$: fragment of 11 amino acids of the sequence Nt-GSNKGAIIGLM-Ct (SEQ ID NO 1) of the APP peptide.
- Sc $AC_{25-35}$: or Sc Aβ, control peptide comprising the 11 amino acids of $A\beta_{25-35}$ in a random order of the sequence Nt-MAKGINGISGL-Ct (SEQ ID NO 2).
- YMT: Y-maze spontaneous alternation Test.
- PAT: Passive Avoidance Test or step-through passive avoidance test.
- ORT: Object Recognition Test.
- WMT: Morris Water Maze Test.
- icv: intracerebroventricular.
- i.p.: intraperitoneal.
- CNS: Central Nervous System.
- Iba-1: ionised calcium-binding adapter molecule 1.
- GFAP: Glial Fibrillary Acidic Protein.
- RaD: stratum radiatum (Rad).
- Mol: stratum moleculare (Mol).
- PoDG: Polymorphic layer of the dentate gyrus.
- LPtA: lateral parietal association area (LPtA).

1. Materials and Methods

The animal experiments were conducted in accordance with the provisions of the European Union directive No. 2010/63 and were duly authorised by the National Ethics Committee (CCNE) of the French Republic.

1.1. Animals

The in vivo experiments were carried out on male Swiss CD-1 (RjOrl:SWISS) mice or C57Bl/6j mice (Janvier, Le Genest-Saint-Isle, France) aged 7 to 9 weeks. The animals were housed in groups of 8-10 individuals in plastic cages with free access to food and drink in a controlled environment (23±1° C., 40-60% humidity, 12-hour day/night cycle). All experiments were conducted with the Swiss mice, except for the hamlet test (see below) which was conducted with C57Bl/6j genotype mice.

1.2. Test Compounds and Peptides

Stock Solutions of Memantine and FENM (Test Compounds).

Memantine hydrochloride was used (Sigma-Aldrich, Saint-Quentin-Fallavier, France). FENM hydrochloride (FENM HCl) was synthesised by M2i Life Sciences (Saint-Cloud, France). Stock solutions of the compounds were obtained by solubilisation in NaCl buffer (0.9%, vehicle) at a concentration of 2 ng/mL which corresponds to a dose of 10 mg/Kg per 100 μL. The stock solutions were stored at 4° C. for up to 2 weeks.

Stock Solution of Amyloid Peptide [25-35]; Formation of Oligomers.

The amyloid peptide [25-35], denoted $A\beta_{25-35}$ (suppliers: Polypeptide, Illkirch, France or Eurogentec, Angers, France), was solubilised in sterile distilled water at a concentration of 3 mg/mL, and the resulting stock solution was aliquoted and stored at −20° C. until use.

Injection of the vehicle solution (distilled water) gave the same lack of effect as the injection of Sc Aβ (control peptide), which comprises the same amino acids as $A\beta_{25-35}$ in a random order and does not oligomerise.

Oligomers of $A\beta_{25-35}$ were formed as described by Maurice et al. (1996), when incubated at 37° C. for 4 days. The vehicle solution or the control peptide were subjected to the same treatment before administration.

Administration to Animals

The test compounds (memantine, FENM HCl) were administered to the animals intraperitoneally in a dose range of 0.1 to 10 mg/Kg.

3 μL of $A\beta_{25-35}$ oligomer solution (the vehicle, sterile distilled water, or Sc Aβ) was administered to the mice by intracerebroventricular (icy) injection, as described by, inter alia, Maurice et al. (1996), Meunier et al. (2006) or Villard et al. (2009).

1.3. Experimental Designs: Symptomatic Treatment and Neuroprotection

The icy injection model of $A\beta_{25-35}$ oligomers is a well-known model in the prior art. $A\beta_{25-35}$ oligomers are known to be cytotoxic to neuronal cells in mice and to induce spatial and working memory impairment. This deficit is accompanied by the generation of mitochondrial stress, oxidative stress and cell apoptosis, in particular in the hippocampus, and by inflammation of the central nervous system. The $A\beta_{25-35}$ peptide is also included in the $A\beta_{1-40}$ or $A\beta_{1-42}$ peptide and autoantibodies against these short fragments have been detected in humans (Gruden et al., 2007). Furthermore, the model has remarkable predictive validity compared to studies with the most widely used transgenic mouse models of Alzheimer's disease (Maurice et al., 2013; Rodriguez-Cruz et al., 2017). Thus, although the onset of the disease is rapid, this model is considered a relevant screening model for the neuroprotective activity of compounds, and in particular a relevant first-line model for Alzheimer's disease. At least one molecule that has been studied mainly on this model (Villard et al., 2009, 2011) is proving to be effective in clinical trials (Hampel et al., 2020) and is now in phase 3.

FIG. 1 is a diagrammatic description of the sequence of the different tests according to the day of icy administration of the $A\beta_{25-35}$ oligomers and the test compounds.

The test compounds were tested for their ability to decrease the cognitive symptoms of $A\beta_{25-35}$ oligomer-induced neurodegeneration, i.e. their ability to provide symptomatic anti-amnestic treatment (FIGS. 1A and 1B). In brief, to test the symptomatic effect of the test compounds, they were administered 8 days after the icy injection of the $A\beta_{25-35}$ oligomers, 30 minutes before the YMT and PAT memory tests were conducted or 30 minutes before the test, but after the training session, in the case of the MWT or ORT (FIG. 1A). The Hamlet Test® (FIG. 1B) involves a 2-week training session (4 hr/day) followed by a test (max. 10 min) under water deprivation conditions and under normal conditions; the $A\beta_{25-35}$ peptide is injected after this first test. After one week, the compounds are administered and a second test under water deprivation conditions and under normal conditions is performed 30 min after injection. This test measures spatial-temporal disorientation, a major warning sign in Alzheimer's disease (Crouzier et al., 2018).

The neuroprotective effect of the compounds, i.e. the ability thereof to protect cells from $A\beta_{25-35}$ oligomer neurotoxicity and neurodegeneration, is also tested (FIG. 10). The test compounds are thus administered on the same day as the injection of the $A\beta_{25-35}$ oligomers and are continued to be administered on a daily basis up to day 7 after the injection of the oligomers, at which time the mice are subjected to the YMT, PAT, MWT or ORT. The brain's anatomy is analysed and neuronal cells are counted by immunohistochemistry on mice sacrificed at D13. The biochemical analyses for the quantification of markers of oxidative stress and apoptosis were carried out at D16 on a group of mice that had been subjected to the WMT (FIG. 10).

Thus, in one case, the $A\beta_{25-35}$ oligomers were allowed to exert their neurotoxicity and induce neurodegeneration before the treatment was implemented, whereas in the other case, the ability of the compounds to prevent this cascade of events and thus prevent neurodegeneration and cell death was assessed.

1.4. Cognitive/Behavioural Tests

T-Maze Spontaneous Alternation Test (YMT)

The spontaneous alternation test was used to assess spatial working memory (very short-term memory) in rodents. The maze was made of grey opaque polyvinylchloride (PVC). Each arm was 40 cm long, 13 cm high, 3 cm wide at the bottom, and 10 cm wide at the top. The arms converged towards one another at an equal angle between the different arms. In brief, each mouse was placed at the end of one arm and allowed to move freely during an 8 min session. The mouse's entries into each arm, including the arm at whose end it was placed, are recorded. An alternation is defined as the animal's successive entry into three different arms. The number of maximum alternations is thus the total number of entries into each arm minus 2 and the percentage of alternation was calculated according to the formula:

% Alt=number of actual alternations/maximum number of alterations×100

The parameters measured included the percentage of alternations (memory index) and the total number of entries into the arms of the maze (exploration index, Maurice et al., 1994, 1996; Meunier et al., 2006, 2013; Villard et al., 2009, 2011). Data from the animals showing extreme behaviour (percentage of alternation <25% or >90%, or a number of entries less than 10) were excluded from the calculations. The attrition rate was routinely 5%. Under normal conditions, a mouse will spontaneously alternate exploring each of the arms. A mouse with impaired memory and/or orientation abilities will have a lower percentage of alternations.

Passive Avoidance Test (PAT)

This test measures non-spatial (contextual) long-term memory. The apparatus used for this test was a box with two compartments (15×20×15 cm high), one illuminated with white PVC walls and the other in the dark with black PVC walls and a grid floor. A guillotine door separated the compartments. A 60 W lamp was positioned 40 cm above the box and illuminated the white compartment. Electric shocks (0.3 mA for 3 s) could be delivered to the grid floor using a generator (Lafayette Instruments, Lafayette, USA). The test comprised a training session and a test session. The guillotine door was closed during the training session. Each mouse was placed in the white compartment. After 5 seconds, the door was raised. When the mouse entered the darkened compartment and placed all four feet in contact with the grid floor, the door was closed and the electric shocks were delivered for 3 seconds. The time taken by the mouse to re-enter the darkened compartment (STL-Tg) and the number of vocalizations were recorded. The test session was conducted 24 hours after the training session. Each mouse was placed back into the illuminated white compartment. After 5 s the door was raised, the step-through latency (STL-R), i.e. the time it took the mouse to enter the darkened compartment, was measured. The maximum duration was 300 s. Mice with a STL-Tg>30 s or a STL-Tg and a STL-R<10 s were not considered for the test. The attrition rate was routinely 5% (Meunier et al., 2006, 2013; Villard et al., 2009, 2011). A mouse with impaired memory abilities will have a lower STL-R than a mouse with normal abilities.

Object Recognition Test

This test is used to assess recognition memory abilities (Rodriguez Cruz et al., 2017; Maurice et al., 2019). The mice were each placed in a square arena (50×50 $cm^2$). In session 1, the mice were allowed to acclimatise to the environment for 10 minutes. In session 2, 24 hours after session 1, two identical objects were placed at ¼ (position 1) and % (position 2) along one of the diagonals of the arena. The exploratory behaviour, activity and position of the animal's nose were recorded for 10 minutes (Nosetrack® software, Viewpoint, Lissieu, France). The number of contacts with the objects and the duration thereof were measured. In session 3, one hour after session 2, the object in position 2 was replaced by a novel object that is different in shape, colour and texture. The exploratory behaviour of each mouse was then also recorded for 10 minutes. Animals showing no contact or less than 10 contacts with an object were discarded from the study.

An exploration index was calculated using to the following formula:

$$\text{Exploration index} = \frac{\text{number (or duration) of contacts with object 2}}{\text{total number (or duration) of contacts with the two objects}}$$

This test is based on the innate exploratory behaviour of mice. It is used to measure recognition memory which involves many areas of the brain. A mouse with impaired memory abilities will be less likely to prefer object 2 in its exploratory behaviour.

Spatial Learning (Morris Water Maze) Test

This test is used to assess long-term spatial reference memory. This test is well known in the prior art and is described in particular by Rodriguez Cruz et al. (2017) and Maurice et al. (2019). It consists of two phases, an acquisition phase and a test phase. The pool was circular in shape (140 cm in diameter) and a 10 cm platform was immersed under the water's surface during the acquisition phase. Markers were placed around the pool to help the animals find their way. The animals' swimming behaviour was recorded (Videotrack® software, Viewpoint), and the trajectories, latencies and distances covered were measured. The acquisition phase comprised sessions of 3 swims per day for 5 days. The start position of the animal was randomly selected from the cardinal points north, south, east and west. Each animal was allowed 90 seconds to find the submerged platform in the middle of the north-eastern quadrant, the water being made opaque by a suspension of whiting powder. The animals were left on the platform for 20 seconds. Animals that did not find the platform after 90 seconds were placed on the platform and also left there for 20 seconds. Median latency (time taken to find the platform) was calculated for each training day and expressed for the group as the mean latency±standard deviation. A retention probe test was performed 72 hours after the last training session. The platform was removed in this test. Each mouse was left in the water for 60 seconds and its swimming behaviour was recorded. The time spent in the north-eastern quadrant, which originally contained the platform (T), was measured and compared to the average time spent in the other quadrants (o).

A mouse with impaired spatial reference memory abilities will spend less time (as a proportion of the time spent in the other quadrants) in the quadrant that contained the platform during the training phases, or even no significantly greater amount of time than the chance level (15 seconds).

Topographic Memory, Hamlet Test

This test is designed to measure the topographic memory of mice in a complex environment. It is based on the familiarisation of the animal with a complex and enriched environment, and on learning, in this enriched context, through the acquisition of superior memory and social functions (Crouzier et al., 2018).

The Hamlet Test® device, with a diameter of 1.2 m, comprises a central square (the agora) and streets that radiate out therefrom and lead to functionalised compartments or houses that allow a physiological function to be met or that enrich the environment. The walls and streets of the hamlet were made of infrared-transparent PVC, the test room was uniformly lit (200 Lux), infrared diodes were placed under the floor of the hamlet and an infrared camera recorded the behaviour of the animals. The agora served as a meeting place and starting point for training and testing sessions. The houses encoded basic physiological functions and contained either pellets (Eat house), water (Drink house), a Novomaze® (Viewpoint) maze (Hide house), a running wheel (Run house) or a separation grid isolating a stranger mouse (Interact house).

This test was described by Crouzier et al. (2018 a and b). In brief, animals from the same cage were placed in the hamlet for 4 hours per day during the two-week training period. Topographic memory was tested during a test phase (PTO), 72 hours after the last training session, after the mice had been deprived of water (bottle removed the evening before, i.e. 15 hours before the test). The performance levels of the animals in reaching the Drink house were compared to the performance levels of the same animals retested the next day without water deprivation. The animals were placed individually in the hamlet for a 10-minute session. The exploratory behaviour was recorded alongside the time taken to find the Drink house and the number of errors made (number of entries into a street not leading to the Drink house). The oligomerised $A\beta_{25-35}$ peptides or the control were injected 2 hours after the test phase and the test compounds (FIG. 1B). The test phase was reiterated after 7 days. A disorientation index (DI) was calculated for each variable (time to find the drink house, number of errors):

$$DI = \frac{\text{performance before injection of } A\beta 25-35 \text{ oligomers}}{\text{performance after injection of } A\beta 25-35 \text{ oligomers}} - \frac{\text{performance before injection of the vehicle}}{\text{performance after the injection of the vehicle}}$$

1.5. Biochemical Analyses

Lipid Peroxidation in Membranes

As shown in FIG. 1C, the mice were sacrificed after the behavioural test by decapitation 15 days after the $A\beta_{25-35}$ injection. Their brains were removed, and the hippocampi were isolated, weighed and frozen at −80° C. awaiting biochemical analysis.

The amount of hydroperoxide present in the samples was measured by quantifying the $Fe^{3+}$-xylenol orange complex: in an acidic medium, hydroperoxides oxidise the $Fe^{2+}$ to $Fe^{3+}$. The latter forms a coloured complex with xylenol orange, the formation whereof was quantified by measuring its absorbance at 580 nm.

After thawing, the hippocampi were homogenised in cold methanol (1/10 w/v), centrifuged at 1000 g for 5 min and the supernatant was collected. The homogenates were added to a solution containing $FeSO_4$ (0.25 mM), $H_2SO_4$ (25 mM), and xylenol orange (0.1 mM) and incubated for 30 min at ambient temperature. The absorbance at 580 nm ($A_{580}1$) was measured and 10 µl of cumene hydroperoxide (CHP, 1 mM) was added and the entirety was incubated for 30 min at ambient temperature. The absorbance at 580 nm was measured again ($A_{580}2$). The level of lipid peroxidation was determined in CHP equivalent (CHP eq.) using the formula:

$$CHP\,eq. = \frac{A_{580}1}{A_{580}2} \times [CHP\,(n\text{mol})] \times \text{dilution factor}$$

CHP eq. is expressed per mass of tissue and presented as a percentage of the control group value.

ELISA Tests, Quantification of Inflammation and Apoptosis Markers

Interleukin 6 (IL-6), a cytokine inflammatory marker, and the levels of the apoptosis markers Bcl2 and Bax proteins were measured in mouse hippocampi by the ELISA tests listed in Table 1 hereinbelow. Bcl2 is often referred to as an anti-apoptotic marker and Bax as a pro-apoptotic marker. Both hippocampi of 6-8 animals per condition were used. The tissues were homogenised after thawing in cell lysis buffer (1 mL, 3 IS007, Cloud-Clone) and sonicated on ice (2×10 s). After centrifugation (10,000 g, 5 min, 4° C.), the supernatants containing the markers to be measured were aliquoted and stored at −80° C. until the ELISA test was carried out according to the supplier's instructions. The results are expressed in ng of marker per mg of total protein and as a percentage of the control (mice not intoxicated with $A\beta_{25-35}$ and not treated with the test compounds).

TABLE 1

| Marker | Supplier | Reference |
|---|---|---|
| IL-6 | Cloud-Clone Corp | SEA079MU |
| Bax | Cloud-Clone Corp | SEB343MU |
| Bcl-2 | Cloud-Clone Corp | SEA778MU |

1.6. Immunohistochemical Analyses

Preparation of Tissue Sections

As shown in FIG. 10, on day 13, for each experimental condition, 5-6 mice were euthanised to conduct these studies. They were previously anaesthetised by i.p. injection of 200 μL of a solution of ketamine (80 mg/Kg) and xylazine (10 mg/Kg), then the tissues were fixed by intracardiac perfusion of 50 mL of a saline solution followed by 50 mL of Antigenfix® fixative (Diapath). The samples were kept for a further 48 hours in the fixative at 4° C., and then the mouse brains were stored in a 30% sucrose solution in PBS, before being sliced.

Slices were taken of each area of the brain, in particular the cortex, the nucleus basalis magnocellularis and the hippocampus (i.e. between bregma +1.8 and bregma −2.8 according to the stereotaxic coordinates of the mouse brain, Paxinos et al., 2004). Serial coronal sections with a thickness of 25 μm were cut with a freezing microtome (Microm HM 450, Thermo Fisher) and stored at −20° C. in a cryoprotective solution.

Quantification of Viable Neurons in Area CA1

In Alzheimer's patients, a decrease in neurons has been reported in the CA1 region (and to a lesser extent in the CA3 region). Such a decrease is also observed in mouse models of the icy injection of $A\beta_{25-35}$ oligomers. In order to quantify viable neurons in the CA1 region of the mouse hippocampus, the corresponding sections were stained with cresyl violet (0.12%, Sigma-Aldrich), dehydrated with ethanol, treated with xylene and mounted with a mounting medium (Mountex medium, BDH Laboratory Supplies) and dried at 24° C. at ambient temperature. The images were recorded and analysed (Nanozoomer virtual microscopy system, Hamamatsu, Massy, France). The thickness of the CA1 area and the number of pyramidal neurons were measured at 20× magnification (cell count macro of ImageJ v1.46 software (NIH)). Data is expressed as a number of viable cells per $mm^2$ for 4-6 hippocampal sections per mouse (Rodriguez Cruz et al., 2017; Maurice et al., 2019).

Immunohistochemical Quantification of Inflammation Markers GFAP and Iba-1

Microglial cells are often presented as the macrophages of the CNS. They proliferate and become active in response to a pathological situation. They can secrete cytokines or reactive oxygen species and are thus partially responsible for the excitotoxicity phenomenon. They are also a marker of pathological neuroinflammation. Iba-1 labelling is specific to the microglial cells in the CNS. The GFAP protein is a constituent of astrocyte intermediate filaments and is used as a marker for astrocytes. Astrocytes play a role in the functional and structural support of neurons. However, astrocytes are also involved in neuroinflammation and can produce numerous cytokines that have neurotoxic activity.

Immunohistochemical labelling is carried out in a conventional manner. In brief, rabbit polyclonal anti-Iba-1 antibodies (reference 019-19741, Wako) and mouse monoclonal anti-GFAP antibodies (reference G3893, Sigma-Aldrich) diluted 250-fold and 400-fold respectively were used to label the microglial cells and astrocytes. Labelling took place overnight at 4° C. Hybridization with secondary Cy3-coupled anti-rabbit antibodies and secondary Alexa Fluor 488-coupled anti-mouse antibodies, diluted 1000-fold, was carried out for one hour at ambient temperature. The sections were then incubated for 5 min in a 10 ug/mL DAPI solution. After rinsing with PBS, the sections were mounted in a mounting fluid (ProLong, ThermoFischer) and images of each section were taken with a confocal fluorescence microscope (Leica SPE) for different sub-regions of the hippocampus such as the stratum radiatum (Rad), the stratum moleculare (Mol), the polymorphic layer of the dentate gyrus (PoDG) and for the cortex, the lateral parietal association area (LPtA). These regions are known to be sites of $A\beta_{25-35}$ oligomer-induced astrogliosis and microgliosis (Maurice et al., 2019).

1.7. Statistical Analyses

The analyses were carried out using Prism v5.0 (GraphPad Software, San Diego, CA, USA). The data were analysed using one-way variance analyses (ANOVA, F-value), followed by a Dunnett's test. Latencies in the passive avoidance test were analysed by a non-parametric Kruskal-Wallis test (ANOVA (H-value), followed by a Dunn's test. In the Morris water maze test, the time spent in the T or o quadrants was analysed using a one-sample t-test for the data of the probe test vs. 15 s. The same is true for the data from session 3 of the object recognition test, with preference being analysed according to the time spent exploring the object and the number of contacts with the object vs. 50%. Statistical significance levels were: $p<0.05$, $p<0.01$ and $p<0.001$.

2. Results 2.1. Neuroprotection and Prevention of Inflammation, Apoptosis and Oxidative Stress Biochemical Markers of Inflammation, Apoptosis and Oxidative Stress in the Hippocampus.

The neuroprotective effect of memantine and of FENM was assessed at the biochemical level by measuring, in the hippocampus, the level of markers of inflammation (IL-6, FIG. 2A), apoptosis (Bax and Bcl-2, and the Bax/BI-2 ratio, FIG. 2C) and oxidative stress (lipid peroxidation, FIG. 2B).

In the hippocampus of untreated mice intoxicated with $A\beta_{2535}$ oligomers, a significant 83% increase in IL-6 (pro-inflammatory cytokine) levels was observed 5 days after intoxication compared to untreated, non-intoxicated mice, confirming the induction of neuroinflammation by $A\beta_{25-35}$ oligomer intoxication. Treatment of the mice with memantine (0.3 mg/Kg) did not result in a significant decrease in IL-6 levels, compared to intoxicated but untreated mice. Conversely, the IL-6 level observed in the hippocampi of mice treated with FENM was significantly lower than that of untreated, intoxicated mice, and reached levels of the same order as those observed for untreated, non-intoxicated mice. (FIG. 2A). The FENM thus prevented $A\beta_{25-35}$ oligomer-induced inflammation.

As expected (Maurice et al., 2013), no significant increase in the level of the anti-apoptotic protein Bcl2 in the intoxicated groups was observed (not shown). The Bax protein levels were significantly increased as a result of $A\beta_{25-35}$ oligomer intoxication (not shown). This increase was significantly reduced (compared to the intoxicated, untreated group) by memantine (0.3 mg/Kg) and by FENM (0.3 mg/Kg) (not shown). Nonetheless, only the treatment of the mice with FENM (0.3 mg/Kg) significantly decreased the Bax/BcI-2 ratio, which was significantly increased as a result of the $A\beta_{25-35}$ intoxication in mice not treated with FENM (FIG. 2C) and which is known in the prior art as a marker of the apoptotic potential of cells. Thus, only FENM can prevent $A\beta_{25-35}$ oligomer-induced apoptosis as determined by the increased Bax/BcI-2 ratio.

It was also observed that treatment with FENM (0.3 mg/Kg i.p.) maintained the number of viable neurons in the CA1 area of the hippocampus and counteracted the increase in thickness of this area in oligomer-intoxicated mice, whereas untreated intoxicated mice showed a 13% decrease in the number of viable cells in the CA1 area, associated with a 12% increase in the thickness of the CA1 area (not shown). The FENM thus prevented $A\beta_{25-35}$ oligomer-induced cellular and structural alterations of the hippocampus.

In connection with apoptosis, mitochondrial dysfunction is also the source of oxidative stress. Lipid peroxidation is a long-term marker of oxidative stress. As expected, intoxication with $A\beta_{25-35}$ oligomers induced a significant increase (+47%, FIG. 2B) in the level of lipid peroxidation in the hippocampal cells of the intoxicated mice. Memantine (0.3 mg/Kg) did not significantly decrease the level of lipid peroxidation and was thus ineffective in preventing oxidative stress induced by $A\beta_{25-35}$ oligomer intoxication. A level equivalent to that of the control group (non-intoxicated, untreated) and significantly lower than that of the intoxicated but untreated mice was observed in the hippocampus of the mice treated with FENM (0.3 mg/Kg). Thus, compared to memantine, only FENM is able to prevent the oxidative stress observed in intoxicated mice as measured by lipid peroxidation.

Thus, only FENM is able to provide effective neuroprotection (in terms of intensity and statistical significance) against $A\beta_{25-35}$ oligomer-induced apoptosis and inflammation.

Observation of Neuroinflammation by Immunohistochemistry.

$A\beta_{25-35}$ oligomer intoxication induces a large and significant increase (compared to non-intoxicated mice) in GFAP (FIG. 3, astrogliosis) and Iba-1 (FIG. 4, microgliosis) labelling in the cortex (LPtA, +110% and +55% respectively). An increase in GFAP and Iba-1 is also observed in the hippocampus of the intoxicated mice in the three areas studied (Rad, Mol and PoDG); it is significant for GFAP labelling in the Rad (+68%) and Mol (+52%) and for Iba-1 labelling in the Rad (+68%) (FIGS. 3 and 4). Although memantine has a positive effect in the PoDG area, only FENM significantly decreases the astrocytic and microglial response in all of the brain areas tested (FIGS. 3 and 4). Memantine also has no effect on astrogliosis in the Mol (FIG. 3B) or on microgliosis in the cortex (FIG. 4D). Thus, FENM is significantly more effective than memantine in preventing the inflammatory response triggered by $A\beta_{325}$-35 oligomer intoxication.

FENM is thus particularly effective compared to memantine in preventing the development of inflammatory, oxidative stress and apoptosis mechanisms observed in neurodegeneration at the molecular level (biochemical markers) and at the cellular and morphological level in a neuroprotection experimental design.

Furthermore, only FENM procures a significant improvement for all of the markers studied.

2.2. Neuroprotection and Preservation of Cognitive Abilities.

It was then checked whether the specific neuroprotective abilities of FENM detected at biochemical and cellular levels in the brain had an effect on the cognitive abilities of animals treated with FENM, compared to those treated with memantine.

The neuroprotective effects of FENM and of memantine were assessed and compared in cognitive and behavioural tests measuring working memory, intermediate-term memory, recognition memory, long-term spatial memory (learning) and orientation skills. These tests were carried out according to the experimental designs shown in FIG. 10. Unless otherwise specified, memantine and FENM (test compounds) were administered at doses of 0.03; 0.1; 0.3; 1.0 and 3 mg/Kg. The doses tested are thus logarithmically distributed in the dose range tested, which allows the activity profiles of the two molecules to be compared.

Superior Effect of FENM in the Morris Water Maze Test.

This test is an assessment of the long-term spatial memory and learning abilities.

$A\beta_{25-35}$ oligomers induce a loss of learning and long-term memory functions (FIG. 5). In the untreated, non-intoxicated mice (control group), it was found that the mice spent significantly more than 15 s in the training quadrant; a significant difference was also observed between the time spent in the training quadrant compared to the time spent in the other quadrants. Untreated, intoxicated mice spent almost as much time in the other quadrants as they did in the training quadrant and the time spent in the training quadrant was no longer significantly different from 15 s. The administration of memantine at 0.3 mg/Kg did not prevent the impairment of learning and memory functions. In contrast, mice intoxicated but treated with 0.3 mg/Kg FENM maintained their learning and memory abilities since they spent significantly more time in the learning quadrant than in the other quadrants, and this time was significantly greater than 15 s (FIG. 5).

Thus, only FENM provided significant protection of the cognitive abilities of the animals measured by this test.

Superior Effect of FENM in the Passive Avoidance Test

As mentioned in the materials and methods section, this test is a fear motivation test conventionally used to assess intermediate-term memory.

A significant decrease in the latency to re-enter the dark compartment was observed for $A\beta_{25-35}$ oligomer-intoxicated mice compared to non-intoxicated mice (not shown). A protective effect of memantine was only observed at two of the doses tested (0.1 and 1 mg/Kg i.p.). In contrast, it was found that FENM procured neuroprotection as regards memory for all doses tested from 0.1 mg/Kg i.p. up to and including 3 mg/Kg.

FENM was thus more effective in providing neuroprotection than memantine, even at higher doses at which memantine had no effect. FENM was thus more effective in preventing cognitive impairment in the model for neurodegeneration induced by the icy injection of $A\beta_{25-35}$ oligomers.

2.3. FENM Lacks the Amnestic Effect of Memantine at the Same Doses.

As mentioned hereinabove, memantine has been shown to have harmful effects on cognition when administered at high doses, both in animal models and in humans. In this experiment, memantine and FENM were administered at a dose of 10 mg/Kg i.p. and the performance of the mice was tested using the passive avoidance test and the Y-maze with non-intoxicated mice. The results are given in Table 2 hereinbelow:

TABLE 2

| | Vehicle | Memantine (10 mg/Kg i.p.) | FENM (10 mg/Kg i.p.) |
|---|---|---|---|
| Y-Maze | | | |
| Alternation (%) | 70.8 ± 3.8 | 48.8 ± 3.0 *** | 63.7 ± 4.2 |
| Number of entries | 30.8 ± 1.3 | 28.2 ± 2.9 | 32.7 ± 3.4 |
| Passive avoidance | | | |
| Latency (s) | 220.8 ± 39.3 | 56.0 ± 31.1** | 183.0 ± 38.4 |
| N | 8 | 9 | 7 |

ANOVA: $F_{(2, 23)} = 10.3$, $p < 0.001$ for alternation; $F_{(2, 23)} = 0.728$, $p > 0.05$ for the number of entries. Kruskal-Wallis ANOVA: $H = 11.4$, $p < 0.01$ for the passive avoidance test. **$p < 0.0034$ vs. vehicle, Dunnett's test.

The data in Table 2 show a negative effect of memantine on the animal's working and intermediate-term memory. A significant decrease in the number of alternations in the Y-maze and in the latency in the passive avoidance test was observed in animals administered with memantine. It should be noted that the harmful effect of memantine on animal performance during these tests is of the same order of magnitude as that of $A\beta_{25-35}$ oligomers observed, for example, in FIG. 6. Conversely, no significant memory impairment was reported for animals administered with FENM (Table 2).

This absence of amnestic effect is of particular interest because, in addition to the superior neuroprotective effects (and symptomatic effects see below) of FENM, treatments with higher doses than those currently accepted for memantine can be considered, and thus a more effective concentration in the CNS can be obtained, which, together with a higher efficacy, procures a more effective treatment in humans.

2.4. Symptomatic Treatment of Cognitive Impairment with FENM.

To evaluate the symptomatic treatment of cognitive impairment resulting from $A\beta_{25-35}$ oligomer-induced neurotoxicity, the molecules were administered according to the experimental design in FIGS. 1 (A) and (B). Memantine is known to procure symptomatic improvement of memory impairment in animal models, but is disappointing in humans; the effects thereof have been compared with those of FENM. The anti-amnestic effects of FENM following $A\beta_{25-35}$ oligomer intoxication were confirmed in all behavioural tests conducted (Y-maze, passive avoidance, object recognition (not shown), Morris water maze (not shown)). Unless otherwise specified, memantine and FENM (test compounds) were administered at doses of 0.1; 0.3; 1.0; 3 and 10 mg/Kg. The doses tested are thus logarithmically distributed in the dose range tested, which allows the activity profiles of the two molecules to be compared.

In general, it was found that FENM is effective over a wider dose range than memantine, and in particular at the higher doses in the range. For example, treatment with FENM was superior in the Y-maze test (FIG. 6) as it was effective at all doses tested from 0.1 mg/Kg, whereas memantine was only effective at 0.3 mg/Kg in restoring an Alt % that was significantly different to untreated, intoxicated mice.

In the passive avoidance test (FIG. 7), a significant improvement in cognitive impairment by memantine was observed at the 0.3 mg/Kg memantine dose only. Moreover, memantine worsens the cognitive symptoms of intoxicated mice when injected at 10 mg/Kg. In contrast, FENM is effective at 0.1; 0.3 and 1 mg/Kg and does not exert an aggravating effect on amnestic symptoms as observed in the case of treatment with memantine (FIG. 7).

The effects of the symptomatic treatment with memantine and FENM on $A\beta_{325}$-35 oligomer-induced memory impairment were also compared in the hamlet test. This test assesses complex memory processes in animals including topographic memory, spatial orientation and learning. The test compounds were administered to the mice for this test at the dose of 0.3 mg/Kg. For the FENM-treated group, the disorientation indexes calculated for errors and latency were reduced to the level of those of the untreated, non-intoxicated mice, but not for the memantine-treated group of animals (FIG. 8).

FENM is thus also more effective in the symptomatic treatment of memory impairment induced by neurodegeneration and can be used at higher doses where memantine is ineffective or even harmful to memory. Moreover, FENM helps maintain complex memory processes (hamlet test), which is not possible with memantine.

3. Conclusions

The experimental data thus show that FENM, unlike memantine, is effective in inducing neuroprotection, which is detected at both the biochemical and cellular levels, against events underlying CNS cell death and neurodegeneration. This neuroprotection leads to the prevention of cognitive impairment in animals. The neuroprotection procured by FENM treatment is not observed with memantine. Moreover, FENM lacks the amnestic effects of memantine when administered in high doses and remains effective at these doses for symptomatic treatment. These data thus show that FENM is of particular interest for preventive (neuroprotective) and symptomatic treatments for neurodegenerative pathologies. The data obtained show a completely atypical and unpredictable behaviour of FENM with respect to the dose ranges found to be effective and the biological effects obtained with memantine in animal models.

REFERENCES

Arndt, J. W., Qian, F., Smith, B. A. et al. Structural and kinetic basis for the selectivity of aducanumab for aggregated forms of amyloid-β. Sci Rep 8, 6412 (2018).

Beaurain M., Salabert A. S., Ribeiro M. J., Arlicot N., Damier P., Le Jeune F., Demonet J. F., Payoux P. Innovative Molecular Imaging for Clinical Research, Therapeutic Stratification, and Nosography in Neuroscience. Frontiers in Medicine, 2019, 6:268. Creeley C, Wozniak D F, Labruyere J, Taylor G T, Olney J W. Low doses of memantine disrupt memory in adult rats. J Neurosci. 2006; 26(15):3923-3932. doi:10.1523/JNEUROSCI.4883-05.2006

Crouzier L, Gilabert D, Rossel M, Trousse F, Maurice T. Topographical memory analyzed in mice using the Hamlet Test, a novel complex maze. Neurobiol Learn Mem. 2018; 149:118-134.

Crouzier L, Maurice T. Assessment of topographic memory in mice in a complex environment using the Hamlet test. Current Protoc Mouse Biol. 2018; 8:e43.

Gruden M A, Davidova T B, Malisauskas M, Sewell R D, Voskresenskaya N I, Wilhelm K, Elistratova El, Sherstnev V V, Morozova-Roche L A Differential neuroimmune markers to the onset of Alzheimer's disease neurodegeneration and dementia: autoantibodies to Abeta ((25-35)) oligomers, S100b and neurotransmitters. J Neuroimmunol. 2007 May; 186(1-2):181-92. Epub 2007 May 2.

Knight R, Khondoker M, Magill N, Stewart R, Landau S: A Systematic Review and Meta-Analysis of the Effectiveness of Acetylcholinesterase Inhibitors and Memantine in Treating the Cognitive Symptoms of Dementia. Dement Geriatr Cogn Disord 2018; 45:131-151. doi: 10.1159/000486546.

Liu C C, Liu C C, Kanekiyo T, Xu H, Bu G. Apolipoprotein E and Alzheimer disease: risk, mechanisms and therapy [published correction appears in Nat Rev Neurol. 2013. doi: 10.1038/nmeurol.2013.32. Liu, Chia-Chan [corrected to Liu, Chia-Chen]]. Nat Rev Neurol. 2013; 9(2):106-118.

Maurice T, Hiramatsu M, Itoh J, Kameyama T, Hasegawa T, Nabeshima T. Behavioral evidence for a modulating role of sigma ligands in memory processes. 1. Attenuation of dizocilpine (MK-801)-induced amnesia. Brain Res. 1994; 647: 44-56.

Maurice T, Lockhart B P, Privat A. Amnesia induced in mice by centrally administered β-amyloid peptides involves cholinergic dysfunction. Brain Res. 1996; 706:181-93.

Maurice T, Mustafa M H, Desrumaux C, Keller E, Naert G, de la C. Garcia-Barceló M, Rodriguez Cruz Y, Garcia Rodriguez J C. Intranasal formulation of erythropoietin (EPO) showed potent protective activity against amyloid toxicity in the Aβ25-35 nontransgenic mouse model of Alzheimer's disease. J Psychopharmacol. 2013; 27; 1044-57.

Maurice T, Voile J N, Strehaiano M, Crouzier L, Pereira C, Kaloyanov N, Virieux D, Pirat J L. Neuroprotection in non-transgenic and transgenic mouse models of Alzheimer's disease by positive modulation of al receptors. Pharmacol Res. 2019; 144:315-330.

Meunier J, leni J, Maurice T. The anti-amnesic and neuroprotective effects of donepezil against amyloid $\beta_{25-35}$ peptide-induced toxicity in mice involve an interaction with the al receptor. Br J Pharmacol. 2006; 149: 998-1012.

Meunier J, Villard V, Givalois L, Maurice T. The γ-secretase inhibitor 2-[(1R)-1-[(4-chlorophenyl)sulfonyl] (2,5-difluorophenyl)amino]ethyl-5-fluorobenzenebutanoic acid (BMS-299897) alleviates $A\beta_{1-42}$ seeding and short-term memory deficits in the $A\beta_{25-35}$ mouse model of Alzheimer's disease. Eur J Pharmacol. 2013; 698:193-9.

Paxinos G, Franklin K B J. The Mouse Brain in Stereotaxic Coordinates. Academic Press, San Diego, CA, USA. 2004.

Pike C J, Walencewicz A J, Glabe C G, Cotman C W. In vitro aging of beta-amyloid protein causes peptide aggregation and neurotoxicity. Brain Res. 1991 Nov. 1; 563(1-2):311-4.

Rodriguez Cruz Y, Strehaiano M, Rodríguez Obaya T, Garcia Rodriguez J C, Maurice T. An intranasal formulation of erythropoietin (Neuro-EPO) prevents memory deficits and amyloid toxicity in the APPSwe transgenic mouse model of Alzheimer's disease. J Alz Dis. 2017; 55:231-248.

Stahl H P and Wermuth C G. Handbook of Pharmaceutical Salts: Properties, Selection, and Use Edited by VHCA, Verlag Helvetica Chimica Acta, Zurich, Switzerland, and Wiley-VCH, Weinheim, Germany.

Villard V, Espallergues J, Keller E, Alkam T, Nitta A, Yamada K, Nabeshima T, Vamvakides A, Maurice T. Anti-amnesic and neuroprotective effects of the aminotetrahydrofuran derivative ANAVEX1-41 against amyloid 1125-35-induced toxicity in mice. Neuropsychopharmacology. 2009 34:1552-66.

Villard V, Espallergues J, Keller E, Vamvakides A, Maurice T. Anti-amnesic and neuroprotective potentials of the mixed muscarinic receptor/sigma$_1$ ($\sigma_1$) ligand ANAVEX2-73, a novel aminotetrahydrofuran derivative. J Psychopharmacol. 2011; 25:1101-17. REFERENCE TO A "SEQUENCE LISTING," A TABLE, OR A COMPUTER PROGRAM LISTING APPENDIX SUBMITTED AS AN ASCII TEXT FILE The material in the ASCII text file, name "APIC-67084-Sequence-Listing_ST25.txt", created Nov. 7, 2022, file size 4,096 bytes, is hereby incorporated by reference.

The invention claimed is:

1. A method for inducing neuroprotection and treating excitotoxicity in a human subject diagnosed with a central nervous system pathology selected from the group consisting of tautopathies, synucleopathies, amyloidopathies, Huntington's disease, amyotrophic lateral sclerosis, epilepsy, vascular dementia, Korsakoff's syndrome, alcohol withdrawal, ischaemia, head injury, and stroke, comprising:

administering to the human subject orally at a dose of 10-100 mg per day of 3-(2-fluoroethyl) adamantan-1-amine (FENM) or a pharmaceutically acceptable salt thereof.

2. The method of claim 1, wherein the administering reduces at least one excitotoxicity-linked readout selected from IL-6 level, lipid peroxidation, Bax/Bcl-2 ratio, microgliosis (Iba-1) or astrogliosis (GFAP) in CNS tissue or CSF, relative to baseline.

3. The method of claim 1, wherein the administering reduces neuron loss.

4. The method of claim 1, wherein the administering inhibits hippocampal cell loss in the subject.

5. The method of claim 1, wherein the dose administered to the human subject is a dose of 30-60 mg per day of the 3-(2-fluoroethyl) adamantan-1-amine (FENM) or the pharamaceutically acceptable salt thereof.

6. The method of claim 1, wherein the dose administered to the human subject is a dose of 20-100 mg per day of the 3-(2-fluoroethyl) adamantan-1-amine (FENM) or the pharamaceutically acceptable salt thereof.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Artificial Sequence
<220> FEATURE:
<223> OTHER INFORMATION: Synthetic construct fragment of APP (a beta
      25-35)

<400> SEQUENCE: 1

Gly Ser Asn Lys Gly Ala Ile Ile Gly Leu Met
1               5                   10


<210> SEQ ID NO 2
<211> LENGTH: 11
<212> TYPE: PRT
<213> ORGANISM: Artificial Sequence
<220> FEATURE:
<223> OTHER INFORMATION: Synthetic construct scrambled A beta

<400> SEQUENCE: 2
```

-continued

```
Met Ala Lys Gly Ile Asn Gly Ile Ser Gly Leu
1               5                   10
```